(12) United States Patent
Ojima

(10) Patent No.: US 6,835,746 B2
(45) Date of Patent: *Dec. 28, 2004

(54) TAXOID ANTI-TUMOR AGENTS AND PHARMACEUTICAL COMPOSITIONS THEREOF

(75) Inventor: Iwao Ojima, Port Jefferson, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/330,535

(22) Filed: Dec. 30, 2002

(65) Prior Publication Data

US 2003/0232878 A1 Dec. 18, 2003

Related U.S. Application Data

(60) Division of application No. 09/822,842, filed on Apr. 2, 2001, now Pat. No. 6,500,858, which is a continuation-in-part of application No. 09/457,332, filed on Dec. 9, 1999, now Pat. No. 6,458,976, which is a continuation-in-part of application No. 08/608,003, filed on Mar. 4, 1996, now Pat. No. 6,100,411, which is a continuation-in-part of application No. 08/330,956, filed on Oct. 28, 1994, now abandoned.

(51) Int. Cl.[7] ..................... A61K 31/337; C07D 305/14
(52) U.S. Cl. .......................... 514/449; 549/510; 549/511
(58) Field of Search ............................... 549/510, 511; 514/449

(56) References Cited

U.S. PATENT DOCUMENTS

| | | | | |
|---|---|---|---|---|
| 4,960,790 A | 10/1990 | Stella et al. | .................. | 514/449 |
| 5,059,699 A | 10/1991 | Kingston et al. | ............ | 549/511 |
| 5,229,526 A | 7/1993 | Holton | .................. | 549/213 |
| 5,243,045 A | 9/1993 | Holton et al. | .................. | 544/60 |
| 5,284,864 A | 2/1994 | Holton et al. | ............... | 514/449 |
| 5,294,637 A | 3/1994 | Chen et al. | .................. | 562/449 |
| 5,294,737 A | 3/1994 | Ojima | .................. | 562/444 |
| 5,399,726 A | 3/1995 | Holton et al. | ............... | 549/510 |
| 5,430,160 A | 7/1995 | Holton | .................. | 549/510 |
| 5,728,725 A | 3/1998 | Holton et al. | ............... | 514/449 |
| 5,728,850 A | 3/1998 | Holton et al. | ............... | 549/510 |
| 5,739,362 A | 4/1998 | Holton et al. | ............... | 549/510 |
| 5,889,043 A | 3/1999 | Bouchard et al. | ........... | 514/449 |
| 6,096,909 A | 8/2000 | Ojima | .................. | 549/510 |
| 6,100,411 A | 8/2000 | Ojima | .................. | 549/510 |
| 6,458,976 B1 | 10/2002 | Ojima | .................. | 549/510 |
| 6,500,858 B2 | 12/2002 | Ojima | .................. | 514/449 |

FOREIGN PATENT DOCUMENTS

| | | |
|---|---|---|
| EP | 0 558 959 A1 | 9/1993 |
| EP | 0 604 910 | 7/1994 |
| EP | 0 639 577 | 2/1995 |
| WO | WO 94/10996 | 5/1994 |
| WO | WO 94/10997 | 5/1994 |
| WO | WO 94/17050 | 8/1994 |
| WO | WO 94/21250 | 9/1994 |
| WO | WO 96/30356 | 10/1996 |

OTHER PUBLICATIONS

Iwao Ojima et al., "New and Efficient Routes to Norstatine and its Analogs with High Enantiomeric Purity by β–Lactam Synthon Method," *Tetrahedron Letters* 33(39): 5737–5740 (1992).

Iwao Ojima et al., "New and Efficient Approaches to the Semisynthesis of Taxol and its C–13 Side Chain Analogs by Means of β–Lactam Synthon Method," *Tetrahedron* 48(34): 6985–7012 (1992).

(List continued on next page.)

*Primary Examiner*—Ba K. Trinh
(74) *Attorney, Agent, or Firm*—Finnegan, Henderson, Farabow, Garrett & Dunner, L.L.P.

(57) ABSTRACT

Pharmaceutical compositions, methods of administration, and methods of treatment of cancer with new generation taxoids, of formulas (I) and (II), and derivatives thereof, are described:

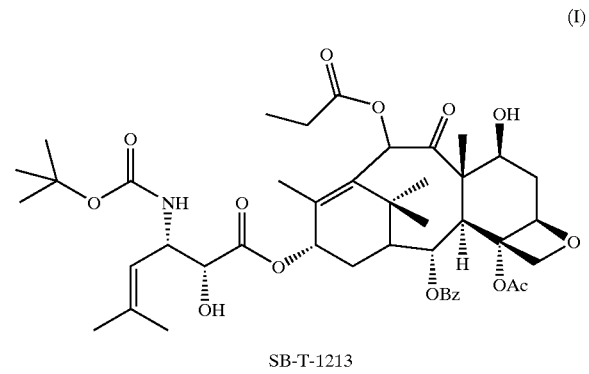

SB-T-1213

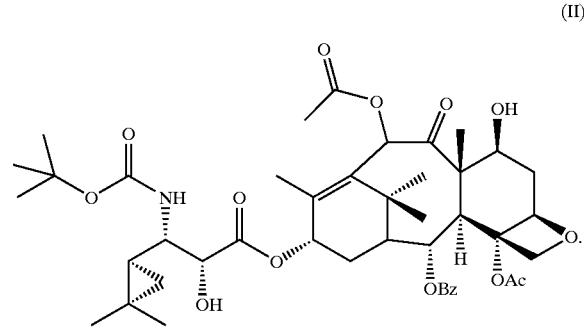

SB-T-1250

18 Claims, No Drawings

OTHER PUBLICATIONS

Iwao Ojima et al., "N–Acyl–3–Hydroxy–β–lactams as Key Intermediates for Taxotere and its Analogs," *Bioorganic & Medicinal Chemistry Letters*, 3(11): 2479–2482 (1993).

Iwao Ojima et al., "A Highly Efficient Route to Taxotere by the β–Lactam Synthon Method," *Tetrahedron Letters*, 34(26): 4149–4152 (1993).

Iwao Ojima et al., "Synthesis and Biological Activity of 3'–Alkyl– and 3'–Alkenyl–3'–Dephenyldocetaxels," *Bioorganic & Medicinal Chemistry Letters*, 4(21): 2631–2634 (1994).

Iwao Ojima et al., "Synthesis and Structure—Activity Relationships of New Antitumor Taxoids. Effects of Cyclohexyl Substitution at the C–3' and/or C–2 of Taxotere (Docetaxel)," *Journal of Medicinal Chemistry*, 37(16): 2602–2608 (1994).

Iwao Ojima et al., "Synthesis and Structure–Activity Relationships of New Second–Generation Taxoids," *Bioorganic & Medicinal Chemistry Letters*, 9(24): 3423–3428 (1999).

Iwao Ojima, "In Vitro Evaluation," *Department of Experimental Therapeutics*, Roswell Park Cancer Institute, Sheet B, May 24, 1994.

Iwao Ojima, "In Vitro Evaluation," *Department of Experimental Therapeutics*, Roswell Park Cancer Institute, Sheet A, Aug. 26, 1994.

Green et al., "Protection for the Hydroxyl Group, Including 1,2– and 1,3–Diols," *Protective Groups in Organic Synthesis*, $2^{nd}$ Edition, pp. 10–12 (1991).

TAXOID ANTI-TUMOR AGENTS AND PHARMACEUTICAL COMPOSITIONS THEREOF

This is a division of U.S. patent application Ser. No. 09/822,842, filed on Apr. 2, 2001, now U.S. Pat. No. 6,500,858, which is a continuation-in-part of U.S. patent application Ser. No. 09/457,332, filed on Dec. 9, 1999, now U.S. Pat. No. 6,458,976B1, which is a continuation-in-part U.S. patent application Ser. No. 08/608,003, filed on Mar. 4, 1996, now U.S. Pat. No. 6,100,411, which is a continuation-in-part of U.S. patent application Ser. No. 08/330,956, filed on Oct. 28, 1994, now abandoned, are incorporated herein by reference, U.S. patent application Ser. Nos. 09/822,842, 08/608,003, and 08/330,956 are incorporated herein by reference.

FIELD OF INVENTION

The present invention relates to new taxoids possessing strong antitumor activities, the precursors of these antitumor taxoids, and pharmaceutical compositions thereof.

BACKGROUND OF THE INVENTION

Taxol (paclitaxel), a complex diterpene, is currently considered the most exciting lead in cancer chemotherapy. Paclitaxel possesses high cytotoxicity and strong antitumor activity against different cancers which have not been effectively treated by existing antitumor drugs. For example, paclitaxel has been approved by FDA in late 1992 for the treatment of advanced ovarian cancer and for breast cancer in 1994. Paclitaxel is currently in phase II and III clinical trial for lung cancer and other cancers.

Although paclitaxel is an extremely important "lead" in cancer chemotherapy, it is common that better drugs can be derived from naturally occurring lead compounds. In fact, French researchers have discovered that a modification of the C-13 side chain of paclitaxel brought about a new anticancer agent which seems to have antitumor activity superior to paclitaxel with better bioavailability. This synthetic compound was named "Taxotére (docetaxel)", which has t-butoxycarbonyl instead of benzoyl on the amino group of (2R,3S)-phenylisoserine moiety at the C-13 position and a hydroxyl group instead of acetoxy group at C-10. Docetaxel is currently in phase II and III clinical trials in United States, Europe, and Japan, has shown excellent activity, especially against breast and lung cancers.

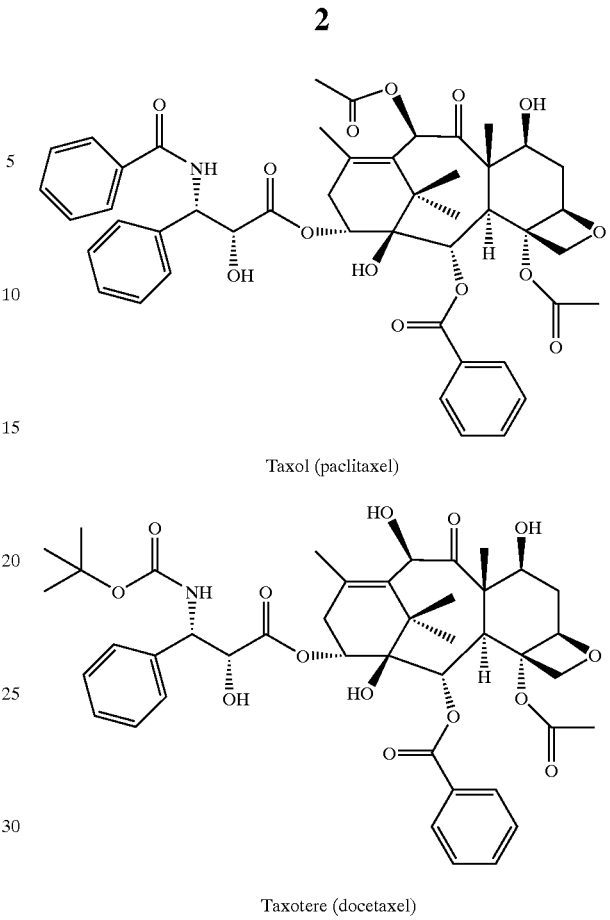

Taxol (paclitaxel)

Taxotere (docetaxel)

A recent report on clinical trials of paclitaxel and docetaxel has disclosed that paclitaxel causes, e.g., nerve damage, muscle pain or disturbances in heart rhythm, whereas docetaxel provokes, e.g., mouth sores and a plunge in white blood cells. Other less serious side effects also exist for these two drugs. Therefore, it is very important to develop new anti-cancer drugs different from these two drugs which have fewer undesirable side effects, better pharmacological properties, improved activity against drug-resistant tumors, and/or activity spectra against various tumor types.

It is an objective of the present invention to develop such new anti-tumor agents of paclitaxel class, i.e., taxoids, which have distinct structural differences from those of paclitaxel and docetaxel.

It is an object of the present invention to provide a series of new taxoids bearing a 1-propenyl, 2-methyl-1-propenyl, 2-methylpropyl, or trifluromethyl radical at the C-3' position instead of a phenyl group, and which possess strong antitumor activities with better therapeutic profile, in particular against drug-resistant tumors. One of the serious drawbacks of both paclitaxel and docetaxel is the fact that these two drugs possess only a weak activity against drug-resistant tumors, e.g., adriamycin-resistant breast cancer. The new taxoids of the present invention have shown not only stronger antitumor activities against human ovarian, non-small cell lung, colon, and breast cancers than those of the two drugs, but also exhibit more than one order of magnitude better activity against adriamycin-resistant human breast cancer cells than those of the two drugs. Multi-drug-resistance (MDR) is a serious issue in clinical oncology, and thus the new taxoid antitumor agents of this invention will serve as important drugs to overcome this problem.

SUMMARY OF THE INVENTION

One aspect of the invention is a taxoid of the formula (I):

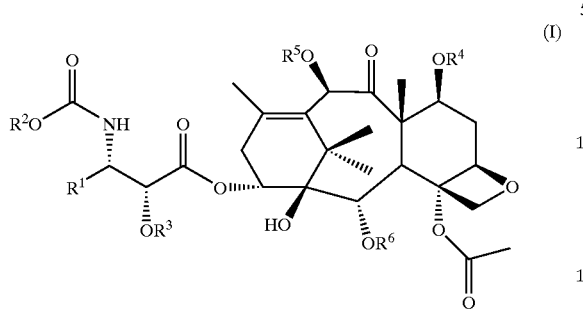

(I)

in which

- $R^1$ is a $C_3$–$C_5$ alkyl or alkenyl or trifluoromethyl radical;
- $R^2$ is a $C_3$–$C_5$ branched alkyl radical;
- $R^3$ and $R^4$ are independently selected from hydrogen and hydroxyl protecting groups including functional groups which increase the water solubility of the taxoid antitumor agent;
- $R^5$ represents a hydrogen or hydroxyl-protecting an acyl or alkoxycarbonyl or carbamoyl group;
- $R^6$ represents an acyl radical, which are useful as antitumor agents or their precursors.

Preferably, $R^1$ is selected from propyl, 2-methyl-1-propenyl, 1-methyl-1-propenyl, 2-methylpropyl, 1-methylpropyl, tert-butyl, cyclopropyl, cyclopropylmethyl, 1-methyl-1-butenyl, 2-methyl-1-butenyl, 3-methyl-1-butenyl, 1-methylbutyl, 2-methylbutyl, isobutyl, 2-methylethyl, 3-methylbutyl, 2-butenyl, or trifluoromethyl radicals;

- $R^2$ is selected from isopropyl, cyclopropyl, isobutyl, sec-butyl, 2-methylpropyl, 3-methylpropyl, tert-butyl, cyclobutyl, cyclopentyl, 1-ethylpropyl, or 1,1-dimethylpropyl radicals;
- $R^5$ is selected from hydrogen, $C_2$–$C_6$ acyl, $C_1$–$C_6$ alkoxylcarbonyl, $C_1$–$C_6$ N-alkylcarbamoyl, or $C_1$–$C_6$ N,N-dialkylcarbamoyl radicals; and
- $R^6$ is selected from benzoyl, fluorobenzoyl, chlorobenzoyl, azidobenzoyl, cyclohexanecarbonyl, acryloyl, crotonoyl, 1-methylacryloyl, 2-methyl-2-butenoyl, or 3-methyl-3-butenoyl radical.

More preferably, $R^5$ is selected from acetyl, propanoyl, cyclopropanecarbonyl, acryloyl, crotonoyl, 3,3-dimethylacryloyl, N-methylcarbamoyl, N-ethylcarbamoyl, N,N-dimethylcarbamoyl, N,N-diethylcarbamoyl, pyrrolidine-N-carbonyl, piperidine-N-carbonyl, morpholine-N-carbonyl, methoxycarbonyl, ethoxylcarbonyl, propoxylcarbonyl, butoxycarbonyl, cyclopentanecarbonyl, or cyclohexanecarbonyl radicals.

These new taxoids (I) are synthesized by the processes which comprise the coupling reactions of the baccatin of the formula (II):

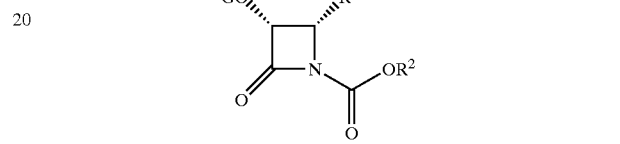

(II)

wherein $G_1$ represents a hydroxyl protecting group, and $R^5$ and $R^6$ have been defined above, with the β-lactams of the formula (III)

(III)

wherein G is a hydroxyl protecting group such as ethoxyethyl (EE), triethylsilyl (TES), (tert-butyl)dimethylsilyl (TBS), and triisopropylsilyl (TIPS), and $R^1$ and $R^2$ have been defined above, in the presence of a base.

Another aspect of the invention is a taxoid of the formula (7):

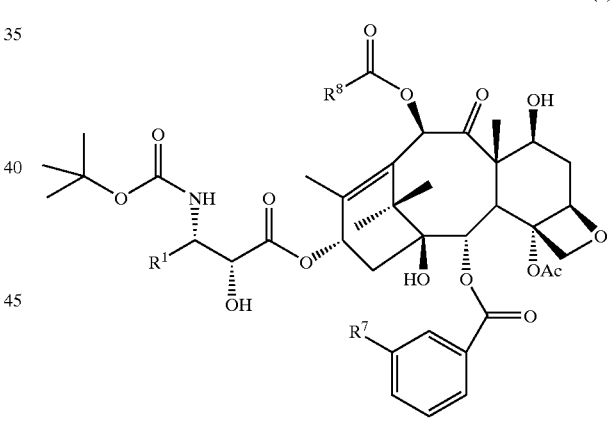

(7)

wherein
$R^1$ is a branched or unbranched $C_3$–$C_5$ alkyl or alkenyl radical, $CF_2H$, or (S)-2,2-dimethylcyclopropyl; $R^8$ is a $C_1$–$C_4$ alkyl radical; and $R^7$ is F, Cl, MeO, vinyl, Me, or $N_3$.

$R^1$ is preferably a branched or unbranched $C_4$ alkyl or alkenyl radical, more preferably $CH_2CH(CH_3)_2$ or $CH=C(CH_3)_2$. $R^7$ is preferably MeO or $N_3$.

In one embodiment, $R^1$ is $CH^2CH(CH_3)_2$, $R^7$ is MeO, and $R^8$ is ethyl. In another embodiment, $R^1$ is $CH=C(CH_3)_2$, $R^7$ is MeO, and $R^8$ is ethyl. In yet another embodiment $R^1$ is $CH=C(CH_3)_2$, $R^7$ is $N_3$, and $R^8$ is ethyl.

The invention also encompasses a method for treating tumors which comprises administering to a patient an effective amount of the taxoid of formula (7). Preferably, the method treats leukemia, melanoma, breast, non-small cell lung, ovarian, and colon cancers.

Yet another aspect of the invention is a pharmaceutical composition having antineoplastic activity containing the taxoid of formula (7) and a physiologically acceptable carrier.

A further aspect of the invention is a method for preparing a taxoid of formula (7), including coupling a baccatin of formula (5) with a β-lactam of formula (6) in the presence of a base, (5)

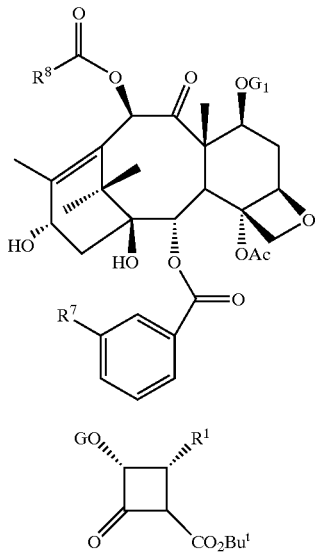

(6)

wherein G and $G_1$, which may be the same or different, each represents a hydroxyl protecting group, and $R^1$, $R^7$, and $R^8$ are as defined for formula (7). Preferably, G and $G_1$ are independently ethoxyethyl (EE), triethylsilyl (TES), (tert-butyl)dimethylsilyl (TBS), or triisopropylsilyl (TIPS).

DETAILED DESCRIPTION OF THE INVENTION

New taxoids of the formula (I) hereinabove are useful as antitumor agents or their precursors. These taxoids possess strong antitumor activities against human breast, non-small cell lung, ovarian, and colon cancers including drug-resistant cancer cells, as well as leukemia and melanoma.

The new taxoids of the formula (I) are synthesized by modifying the baccatins of the formula (II):

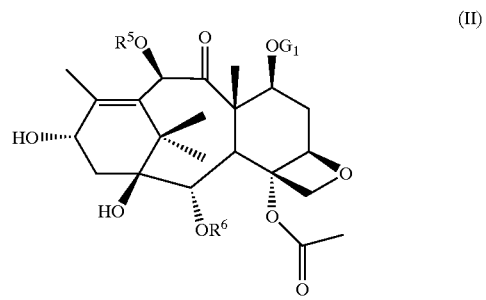

(II)

wherein $G_1$, $R^5$, and $R^6$ have been defined above.

The baccatins (II) are coupled with the β-lactams of the formula (III):

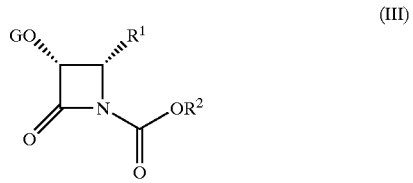

(III)

wherein G, $R^1$, and $R^2$ have been defined hereinabove, to yield the new taxoids (I).

The β-lactams (III) are readily prepared via the β-lactams (IV) which are easily obtained through the chiral enolate-imine cyclocondensation method that has been developed in the present inventor's laboratory as shown in Scheme 1 (Ojima et al., Bioorg. Med. Chem. Lett., 1993, 3, 2479, Ojima et al., Tetrahedron Lett., 1993, 34, 4149, Ojima et al., Tetrahedron Lett. 1992, 33, 5739, Ojima et al., Tetrahedron, 1992, 48, 6985, Ojima, I. et al., J. Org. Chem., 1991, 56, 1681, the disclosures of which are incorporated herein by reference). In this preparation, the β-lactams (IV) with extremely high enantiomeric purities are obtained in high yields. In Scheme 1, R* is a chiral auxiliary moiety which is (−)-trans-2-phenyl-1-cyclohexyl or (−)-10-dicyclohexylsulfamoyl-D-isobornyl, TMS is a trimethylsilyl radical, and the base is lithium diisopropylamide or lithium hexamethyldisilazide and G and $R^1$ have been defined hereinabove.

Scheme 1:

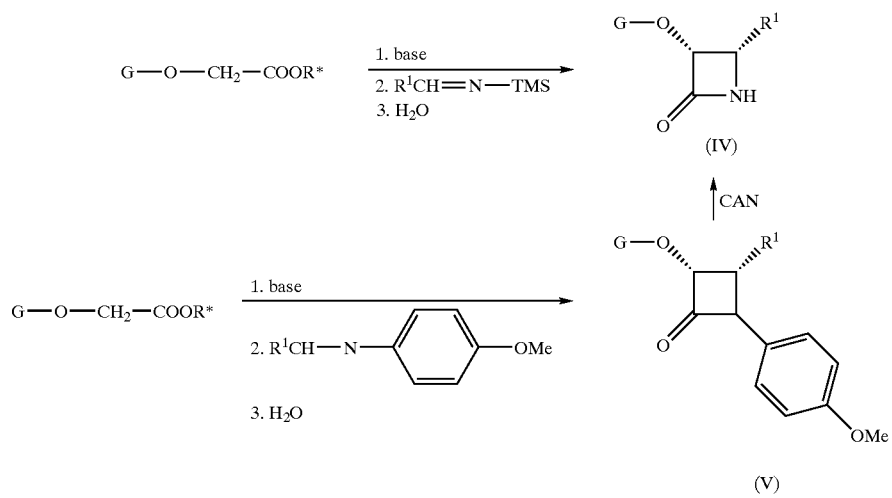

The β-lactams (IV) can be converted to the corresponding N-alkoxycarbonyl-β-lactams (III) in excellent yields by reacting with alkyl chloroformates in the presence of a base (Scheme 2). This transformation is known to those skilled in the art.

The β-lactams (III) are readily used for coupling with the baccatins (II) in the presence of a base, followed by deprotection to give the new taxoids (I) in high yields (Scheme 3).

Scheme 2:

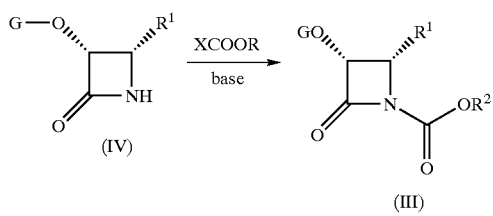

Scheme 3:

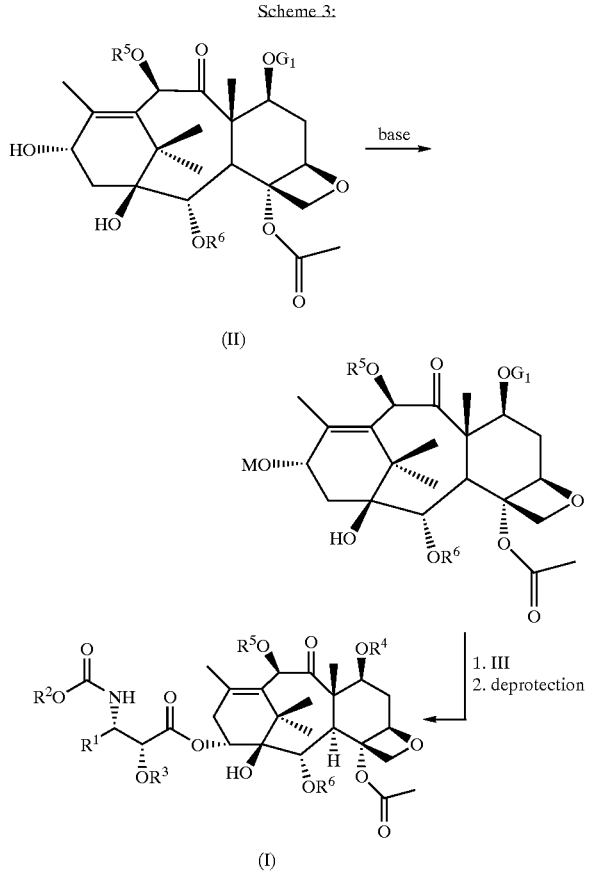

In Schemes 1–3, $R^1$ through $R^6$ have been defined above, M is an alkali metal, and the hydroxyl protecting group $G_1$ is independently selected from methoxylmethyl (MOM), methoxyethyl (MEM), 1-ethoxyethyl (EE), benzyloxymethyl, (β-trimethylsilylethoxy)-methyl, tetrahydropyranyl, 2,2,2-trichloroethoxylcarbonyl (Troc), benzyloxycarbonyl (CBZ), tert-butoxycarbonyl (t-BOC), 9-fluorenylmethoxycarbonyl (Fmoc), 2,2,2-trichloroethoxymethyl, trimethylsilyl, triethylsilyl, tripropylsilyl, dimethylethylsilyl, dimethyl(t-butyl)silyl, diethylmethylsilyl, dimethylphenylsilyl, diphenylmethylsilyl, acetyl, chloroacetyl, dichloroacetyl, trichloroacetyl and trifluoroacetyl.

The coupling reaction of the baccatin (II) and the β-lactams (VI) is carried out via an alkali metal alkoxide of the baccatin (II) at the C-13 hydroxyl group. The alkoxide can readily be generated by reacting the baccatin with an alkali metal base such as sodium hexamethyldisilazide, potassium hexamethyldisilazide, lithium hexamethyldisilazide, sodium diisopropylamide, potassium diisopropylamide, lithium diisopropylamide, sodium hydride, in a dry nonprotic organic solvent such as tetrahydrofuran (THF), dioxane, ether, dimethoxyethane (DME), diglyme, dimethylformamide (DMF), mixtures of these solvents with hexane, toluene, and xylene, in a preferred temperature range from about −100° C. to about 50° C., more preferably at about −78° C. to about 25° C. This reaction is preferably carried out under inert atmosphere such as nitrogen and argon. The amount of the base used for the reaction is preferably approximately equivalent to the amount of the baccatin when soluble bases such as sodium hexamethyldisilazide, potassium hexamethyldisilazide, lithium hexamethyldisilazide, sodium diisopropylamide, potassium diisopropylamide, lithium diisopropylamide are used. The use of a slight excess of the base does not adversely affect the reaction. When heterogeneous bases such as sodium hydride and potassium hydride are used, 5–10 equivalents of the base (to the amount of the baccatin) are preferably employed.

The coupling reaction of the metal alkoxide of the baccatin thus generated with the β-lactam is typically carried out by adding the solution of the β-lactam in a dry organic solvent exemplified above in a preferred temperature range from about −100° C. to 50° C., more preferably at about −35° C. to 25° C. The mixture of reactants is stirred for 15 minutes to 24 hours and the progress and the completion of the reaction is monitored by thin layer chromatography (TLC), for example. When the limiting reactant is completely consumed, the reaction is quenched by addition of a cold brine solution. The crude reaction mixture is worked up using the standard isolation procedures which are generally known to those skilled in the art to give the corresponding taxoid. The proportion of the β-lactam and the baccatin is in a range from 2:1 to 1:2, more preferably approximately 1:1 for purposes of economy and efficiency, but the ratio is not critical for the reaction.

The hydroxyl protecting groups can then be removed by using the standard procedures which are generally known to those skilled in the art to give the desired taxoid derivatives. For example, EE and TES groups can be removed with 0.5 N HCl at room temperature for 36 h, TIPS and TBS groups can be removed by treating with fluoride ion or HF in a non-protic organic solvent, and Troc group can be removed with zinc and acetic acid in methanol at 60° C. for 1 hour without disturbing the other functional groups and the skeleton of the taxoid.

It has been shown that the introduction of 2-methyl-1-propenyl group to the C-3' position of paclitaxel appears to increase the cytotoxicity, especially against drug-resistant cancer cells. Holton and Nadizadeh disclosed in U.S. Pat. No. 5,284,864 (1994) that 3'-dephenyl-3'-isobutenylpaclitaxel (RAH-1) exhibited 4 times better activity than paclitaxel and 7 times better activity than docetaxel against human colon carcinoma cells HCT-116, and also about 20 times better activity than paclitaxel and 9 times better activity than docetaxel against multi-drug resistant phenotype human colon carcinoma cells HCT-116/VM.

We have found that the structural requirements for taxoid antitumor agents to express strong potency are rather strict and unpredictable. For example, 3'-dephenyl-3'-(2- phenylethenyl)docetaxel, bearing 2-phenylethenyl group instead of the isobutenyl group of RAH-1, has dramatically decreased cytotoxicity (>20 times) and 3'-dephenyl-3'-neopentyldocetaxel, bearing neopentyl group which has just one more methyl than isobutenyl group, is virtually not cytotoxic against A121 human ovarian, A549 human non-small cell lung, HT-29 human colon and MCF7 human breast cancer cells. While looking at the structure-activity relationships (SAR) of new taxoids that have different substituents at the C-3' and C-10, we discovered that there are optimum combinations of these two substituents which achieve extraordinarily high activity against drug-resistant cancer cells.

After searching for the best substituent for the C-3' and the C-10 positions by employing many alkyl groups and alkenyl groups by trial and error, we have identified 1-propenyl, 2-methyl-1-propenyl, 2-methylpropyl, and trifluoromethyl groups to be the optimum substituents for the C-3' position, and acyl groups, alkoxycarbonyl groups, and N,N-dialkylcarbamoyl groups to be the optimum substituents for the C-10 position.

For example, 3'-dephenyl-3'-(1-propenyl)-10-acetyldocetaxel (Taxoid Ia) showed a substantially better activity spectrum than that of paclitaxel and docetaxel against human ovarian, human non-small cell lung, human colon, and human breast cancer cells mentioned above (see TABLE 1 in EXAMPLE 32). Moreover, this agent possesses 21 times better activity than paclitaxel and 17 times better activity than docetaxel against the drug-resistant human breast cells MCF7-R, which are mammary carcinoma cells 180 fold resistant to a widely used anticancer drug, adriamycin. In the same assay, Holton's compound RAH-1 showed only marginal activity that was one order of magnitude weaker than that of Taxoid Ia (see TABLE 1 in EXAMPLE 32).

3'-Dephenyl-3'-(2-methyl-1-propenyl)-10-cyclopropanecarbonyldocetaxel (Taxoid IX) showed one order of magnitude better activity than that of paclitaxel and docetaxel against human human breast cancer cells mentioned above (see TABLE 2 in Example 32), and possesses two order of magnitude (142 times) better activity against the drug-resistant human breast cells mentioned above. These extraordinarily high activities are totally unpredictable from the existing SAR studies of paclitaxel and docetaxel, and thus demonstrate the exceptional importance of our discovery.

The taxoids of the formula (I) of this invention are useful for inhibiting tumor growth or regression of tumors in animals including humans and are preferably administered in the form of a pharmaceutical composition including effective amounts of the antitumor agent of this invention in combination with a pharmaceutically acceptable vehicle or diluent.

The pharmaceutical compositions of the antitumor agents of the present invention may be made in any form suitable for desired use, e.g., oral, parenteral or topical administration. Examples of parenteral administration are intramuscular, intravenous, intraperitoneal, rectal, and subcutaneous administration. The vehicle or diluent ingredients should not reduce the therapeutic effects of the antitumor agents of this invention.

Suitable dosage forms for oral use include tablets, dispersible powders, granules, capsules, suspension, syrups, and elixirs. Examples of inert diluents and vehicles for tablets include calcium carbonate, sodium carbonate, lactose and talc. Examples of inert diluents and vehicles for capsules include calcium carbonate, calcium phosphate, and kaolin.

Dosage forms appropriate for parenteral administration include solutions, suspensions, dispersions, and emulsions.

The water solubility of the antitumor agents of the formula (I) may be improved by modifying the C-2' and/or C-7 substituents to incorporate suitable functional groups, such as $R^3$ and $R^4$. In order to increase the water solubility, $R^3$ and $R^4$ can be independently selected from hydrogen and —CO—X—Y, wherein X is selected from —$(CH_2)_n$-(n=1–3), —CH=CH—, cyclohexanediyl, and benzenediyl and Y is selected from —COOH and its pharmaceutically acceptable salts, —$SO_3H$ and its pharmaceutically acceptable salts, —$NR^7R^8$ and its pharmaceutically acceptable salts, the pharmaceutically acceptable ammonium salt —$NR^7R^8R^9$, —$CONR^8R^9$, or —$COOR^9$, in which —$NR^7R^8$ includes cyclic amine radicals selected from pyrrolidinyl, piperidinyl, morphorino, piperazinyl, and N-methylpiperazinyl;

$R^7$ and $R^8$ are independently selected from hydrogen, allyl, $C_1$–$C_6$alkyl, and —$(CH_2)_n$—Z (n=1–3);

$R^9$ is selected from $C_1$–$C_6$alkyl, allyl, and —$(CH_2)_n$—Z (n=1–3), and

Z is selected from —COOH and its pharmaceutically acceptable salts, —$SO_3H$ and its pharmaceutically acceptable salts, —$NR^7R^8$ and its pharmaceutically acceptable salts, and pharmaceutically acceptable ammonium salt —$NR^7R^8R^{10}$, in which $R^{10}$ is selected from hydrogen, allyl, and $C_1$–$C_6$ alkyl.

The preparation of the water-soluble analogs of paclitaxel bearing the functionalized acyl groups described above has been disclosed in Kingston et al., U.S. Pat. No. 5,059,699 (1991); Stella et al., U.S. Pat. No. 4,960,790 (1990), the disclosures of which are incorporated herein by reference, and thus it is not difficult for the people in the art to carry out such modifications.

The following non-limiting examples are illustrative of the present invention. It should be noted that various changes could be made in the examples and processes therein without departing from the scope of the present invention. For this reason, it is intended that the embodiments of the present application should be interpreted as being illustrative and not limiting in any sense.

EXAMPLE 1

(−)-(1R,2S)-2-phenyl-1-cyclohexyl triisopropylsilyloxyacetate

A solution of (−)-(1R,2S)-2-phenyl-1-cyclohexyl hydroxyacetate (851 mg, 3.63 mmol) was prepared through esterification of benzyloxyacetyl chloride with (−)-(1R,2S)-2-phenyl-1-cyclohexanol followed by hydrogenolysis. Then, triisopropylsilyl chloride (840 mg, 4.36 mmol) and imidazole (618 mg, 9.08 mmol) in dimethylformamide (DMF) (1.7 mL) was added and stirred at room temperature for 12–20 hours. The mixture was poured into pentane (25 mL), and washed with water and brine. The combined organic layers were dried over anhydrous $MgSO_4$ and concentrated in vacuo. The crude product was subjected to a purification on a short silica gel column using hexane/chloroform (3/1) as the eluant to give pure (−)-(1R,2S)-2-phenyl-1-cyclohexyl triisopropylsilyloxyacetate (1.35 g, 95% yield) as a colorless oil: $[\alpha]_D^{20}$ −17.1° C. 3.15, $CHCl_3$); IR (neat) 1759, 1730 ("CO) cm$^{-1}$; $^1H$ NMR ($CDCl_3$) δ0.93–0.99 (m, 21H), 1.30–1.62 (m, 4H), 1.72–2.0 (m, 3H), 2.10–2.19 (m, 1H), 2.66 (dt, J=11.5, 4.0 Hz, 1H), 3.90 (d, J=16.6 Hz, 1H), 4.07 (d, J=16.6 Hz, 1H), 5.07 (dt, J=10.6, 4.0 Hz, 1H), 7.16–7.30 (m, 5H). Anal. Calcd for $C_{23}H_{38}O_3Si$: C, 70.72; H, 9.81. Found: C, 70.79; H, 9.85.

EXAMPLES 2–3

N-(4-Methoxyphenyl)-2-alkenylaldimine

To a solution of 0.360 g. (2.9 mmol) of p-anisidine (recrystallized twice from ethanol) in 12 mL of $CH_2Cl_2$ over anhydrous $Na_2SO_4$ was added 0.24 g (3.5 mmol) of 2-butenal (crotonaldehyde) (distilled immediately prior to use) under nitrogen. After 4 hours, $Na_2SO_4$ was filtered off and the solvent removed under vacuum to give N-(4-methoxyphenyl)-2-butenaldimine in quantitative yield, which was used for the synthesis of β-lactam without further purification.

In the same manner, N-(4-methoxyphenyl)-3-methyl-22-butenaldimine was obtained in quantitative yield.

EXAMPLES 4–5

(3R,4S)-1-(4-Methoxyphenyl)-3-triisopropylsilyloxy-4-(1-alkenyl)azetidin-2-one (V)

To a solution of 0.27 mL (1.9 mmol) of diisopropylamine in 10 mL of THF was added 0.76 mL (1.9 mmol) of 2.5M n-butyllithium in hexanes at −10° C. After stirring for 45 minutes, the solution was cooled to −85° C. A solution of (−)-(1R,2S)-2-phenyl-1-cyclohexyl triisopropylsilyloxy-acetate (0.575 g 1.47 mmol) in 10 mL of THF was added via cannula over a period of 1.5 hours. After stirring for an additional hour, a solution of N-(4-methoxyphenyl)-2-butenaldimine (336 mg, 2.2 mmol) in 10 mL of THF was added via cannula over a period of approximately 1 hour. The mixture was stirred for 2 hours and allowed to warm up to room temperature overnight while stirring. The reaction was then quenched with saturated $NH_4Cl$. The aqueous layer was extracted with ethyl acetate (EtOAc) and the combined organic layers were washed with saturated $NH_4Cl$ solution, and brine, and then dried over $MgSO_4$. After the removal of solvent under vacuum, the crude product was obtained, which was purified by flash chromatography on silica gel (hexane:EtOAc=10:1 to 6:1) to afford pure PMP-β-lactam Va (399 mg, 70% yield) as a rust-colored oil. The enantiomeric purity of the PMP-β-lactam Va was determined to 97% ee on the basis of chiral HPLC analysis: $[\alpha]_D=+33.1°$ © 0.27, $CHCl_3$); $^1H$ NMR ($CDCl_3$, 250 MHz) δ1.04–1.16 (m, 21H), 1.76 (dd, J=6.5, 1.3 Hz, 3H), 3.74 (s, 3H), 4.51 (dd, J=8.6, 5.0 Hz, 1H), 5.04 (d, J=5.0 Hz, 1H), 5.59 (ddd, J=15.4, 8.6, 1.3 Hz, 1H, 5.92 (dq, J=15.4, 6.5 Hz, 1H), 6.83 (d, J=9.0, 2H), 7.36 (d, J=9.0 Hz, 2H); $^{13}C$ NMR (63 MHz, $CDCl_3$) d 11.89, 17.63, 17.68, 55.38, 61.89, 77.57, 114.18, 118.48, 126.65, 127.48, 128.34, 128.55, 132.59, 156.03, 165.43.

In the same manner, PMP-β-lactam Vb ($R^1$=2-methyl-1-propenyl) was obtained in 73% yield (93% ee): $[\alpha]_D=+65.7°$ © 1.00, $CHCl_3$); $^1H$ NMR ($CDCl_3$, 300 MHz) δ1.08–1.12 (m, 21H), 1.81 (s, 3 H), 1.86 (s, 3 H), 3.78 (s, 3 H), 4.79–4.84 (dd, J=5.1, 9.9 Hz, 1 H), 5.05–5.07 (d, J=5.1 Hz, 1 H) 5.33–5.36 (bd, J=9.9 Hz, 1 H); $^{13}C$ NMR ($CDCl_3$, 63 MHz) d 11.92, 17.61, 18.33, 26.11, 55.44, 57.56, 76.51, 77.015, 77.52, 114.25, 118.34, 120.15, 128.73, 131.52, 139.14, 156.00, 165.61.

EXAMPLES 6–7

(3R,4S)-3-Triisopropylsilyloxy-4-(1-alkenyl)azetidin-2-one (IV)

To a solution of 260 mg. (0.67 mmol) of N-PMP-β-lactam Va in 20 ml. of acetonitrile at −10° C., was added dropwise a solution of 1.13 g (2.07 mmol) of cerium ammonium nitrate (CAN) in 25 mL of water. The mixture was allowed to stir for 1 hour and then diluted with 50 mL of water. The aqueous layer was extracted with ethyl acetate (2×35 mL) and the combined organic layers were washed with water, 5% $NaHSO_3$, 5% $Na_2CO_3$, and brine. After drying over $MgSO_4$ and concentrating under vacuum, the organic layers afforded the crude product, which was purified on a silica get column using hexane-ethyl acetate as the etuant (hexane:EtOAc=3:1) to give the pure β-lactam IVa ($R^1$=1-propenyl) (124 mg, 65% yield) as a pale yellow viscous oil: $^1H$ NMR ($CDCl_3$, 250 MHz) δ1.04–1.16 (m, 21H), 1.70 (dd, J=6.5, 1.2 Hz, 3H), 4.13 (dd, J=8.7, 4.9, 1H), 4.94 (d, J=4.9 Hz, 1H), 5.51 (ddd, J=14.1, 8.7, 1.2 Hz, 1H), 5.67 (m, 1H), 6.68 (br s, 1H); $^{13}C$ NMR (63 MHz, $CDCl_3$) d 11.80, 17.57, 17.62, 58.14, 79.18, 127.97, 130.64, 170.36.

In the same manner, β-lactam IVb ($R^1$=2-methyl-1-propenyl) was obtained in 94% yield: $^1H$ NMR ($CDCl_3$, 300 MHz) δ1.02–1.10 (m, 21 H), 1.65 (s, 3 H), 1.72 (s, 3 H), 4.36–4.40 (dd, J=4.5, 9.6 Hz, 1 H), 4.91–4.93 (dd, J=2.1, 4.5 Hz, 1 H), 5.23–5.26 (bd, J=9.6 Hz, 1 H), 6.28 (bs, 1 H, NH).

EXAMPLES 8–9

(3R,4S)-1-tert-Butoxycarbonyl-3-triisopropylsilyloxy-4-(1-alkenyl)azetidin-2-one (III)

To a solution of 100 mg (0.35 mmol) of the β-lactam IVa, 0.24 mL (1.75 mmol) of triethylamine, and a catalytic amount of dimethylaminopyridine (DMAP) in 11 mL of $CH_2Cl_2$, was added dropwise at room temperature, 85 mg. (0.38 mmol) of di(tert-butyl) dicarbonate in 2 mL of $CH_2Cl_2$. The mixture was stirred for 1 hour and quenched with saturated $NH_4Cl$ solution. The mixture was diluted with 60 mL of ethyl acetate and the organic layer was washed with brine, dried over $MgSO_4$, and concentrated. The crude product was purified by flash chromatography on silica gel (hexane:EtOAc=4:1) to yield pure N-$^t$BOC-β-lactam IIIa ($R^1$=1-propenyl) as colorless oil (105 mg, 87% yield): $^1H$ NMR ($CDCl_3$, 250 MHz) δ1.02–1.08 (m, 21H), 1.48 (s, 9H), 1.74 (dd, J=6.4, 1.3 Hz, 3H), 4.44 (dd, J=8.6, 5.8 Hz, 1H), 4.94 (d, J=5.8 Hz, 1H), 5.54 (ddd, J=15.4, 8.6, 1.3 Hz), 5.83 (dq, J=15.4, 6.4 Hz, 1H); $^{13}C$ NMR (63 MHz, $CDCl_3$) δ11.76, 17.52, 17.95, 27.97, 61.04, 83.06, 124.80, 132.72, 148.0, 166.07. Anal. Calcd for $C_{20}H_{37}NO_4Si$: C, 62.62, H, 9.72, N, 3.65. Found: C, 62.62; H, 9.63; N, 3.61.

In the same manner, N-$^t$BOC-β-lactam IIIb ($R^1$=2-methyl-1-propenyl) was obtained as a colorless oil in 82% yield: $^1H$ NMR ($CDCl_3$, 300 MHz) δ0.97–1.06 (m, 21 H), 1.48 (s, 9 H), 1.75 (s, 3 H), 1.78 (s, 3 H), 4.72–4.77 (dd, J=5.7, 9.9 Hz, 1 H), 4.94–4.96 (dd, J=5.7 Hz, 1 H), 5.25–5.28 (bd, J=9.9 Hz, 1 H).

EXAMPLES 10–15

7-Triethylsilyl-10-O-substituted 10-deacetylbaccatin III (IIb-g)

To a solution of 1.0 g (1.84 mmol) of 10-deacetylbaccatin III and 375 mg (5.52 mmol) of imidazole in 10 mL DMF was added dropwise 0.9 mL (5.52 mmol) of chlorotriethylsilane (TESCl). The reaction mixture was stirred for 5 hours at room temperature and quenched with water, then diluted with EtOAc. The aqueous layer was extracted with EtOAc and the combined organic layers were washed with water, dried over $MgSO_4$, and concentrated. The crude product was purified by flash chromatography on silica gel (hexane/EtOAc, 1:1) to give 774 mg (64%) of 7-triethylsilyl-10-deacetylbaccatin III (7-TES-DAB) as a white solid: $^1H$ NMR (CDCl$_3$, 250 MHz) δ 0.50 (m, 6 H), 0.97 (m, 9 H), 1.21 (s, 3 H), 1.58 (s, 3 H), 1.73 (s, 3 H), 1.85 (dt, 1 H),1.99 (s, 3 H), 2.23 (s, 3 H), 2.24 (s, 2 H), 2.47 (ddd, 1 H), 3.94 (d, J=7.2 Hz, 1 H), 4.14 (AB, J$_{AB}$=8.4 Hz, 1 H), 4.32 (AB, J$_{AB}$=8.1 Hz, 1 H), 4.41 (d, J=6.3 Hz, 1 H), 4.84 (t, 1 H), 4.94 (d, J=8.4 Hz, 1 H), 5.14 (s, 1 H), 5.19 (s, 1 H), 5.58 (d, J=7.2 Hz, 1 H), 7.40 (t, 2 H), 7.54 (t, 1 H), 8.10 (d, 2 H).

To 77 mg (0.117 mmol) of 7-TES-DAB in 5 mL THF was added 0.12 mL of LiHMDS (1M in THF). The reaction mixture was stirred at −40° C. for 5 minutes, then 0.010 mL (0.117 mmol) of propanoyl chloride (previously distilled) was added. The solution was allowed to warm up at 0° C. over a 30 min period. Then the solvent was removed in vacuo and the crude product was purified by flash chromatography on silica gel (hexane then hexane/EtOAc, 4:1, then 2:1 and 1:1) to afford 60 mg (72%) of 7-triethylsilyl-10-propanoyl-10-deacetylbaccatin III (IIb) as a white solid: [α]$_D^{21}$−68.57° © 1.75, CHCl$_3$); $^1$H NMR (CDCl$_3$, 250 MHz) δ 0.52 (q, 6 H), 0.87 (t, 9 H), 1.02 (s, 3 H), 1.16–1.22 (m, 6 H), 1.55 (s, 9 H), 1.67 (s, 3 H), 1.86 (m, 1 H), 2.19 (s, 3 H), 2.25 (s, 2 H), 2.27 (s, 3 H), 2.42 (m, 3 H), 3.86 (d, J=6.9 Hz, 1 H), 4.12 (AB, J$_{AB}$=8.0 Hz, 1 H), 4.27 (AB, J$_{AB}$=8.0 Hz, 1 H), 4.49 (dd, 1 H), 4.83 (t, 1 H), 4.93 (d, J=9.2 Hz, 1 H),5.61 (d, J=6.9 Hz, 1 H), 6.46 (s, 1 H), 7.43 (t, 2 H), 7.56 (t, 1 H), 8.08 (d, 2 H); $^{13}$C NMR(CDCl$_3$, 63 MHz) δ 5.2, 6,7, 9.2, 9.9, 14.9, 20.1, 22.6, 26.7, 27.6, 37.2, 38.3, 42.7, 58.6, 67.8, 72.3, 74.7, 75.5, 76.5, 77.0, 77.5, 78.7, 80.8, 84.2, 128.5, 129.4, 130.0, 132.6, 133.5, 143.9,167.8, 170.7, 174.5, 202.3. IR (neat, cm$^{-1}$) 2953, 2913, 1789, 1738, 1715, 1681, 1454, 1434, 1392, 1362, 1315, 1175, 1108. HRMS (FAB, DCM/NBA) m/z: Calcd. for C$_{38}$H$_{54}$O$_{11}$SiH$^-$, 715.3513. Found, 715.3552.

In the same manner, the following 7-triethylsilyl-1-O-substituted-10-deacetylbaccatin IIIs were prepared.

7-Triethylsilyl-10-cyclopropanecarbonyl-10-deacetylbaccatin III (IIc)

White solid; [α]$_D^{21}$−61.42° © 7.00, CHCl$_3$); $^1$H NMR (CDCl$_3$, 250 MHz) δ 0.46 (m, 6 H), 0.82 (m, 9 H), 0.97 (s, 3 H), 1.12 (s, 3 H), 1.18 (m, 2 H), 1.60 (s, 3 H), 1.68 (m, 2 H), 1.79 (m, 1 H), 2.12 (s, 3 H), 2.16 (s, 2 H), 2.20 (s, 3 H), 2.40 (m, 1 H), 2.50 (d, 1 H), 3.79 (d, J=6.9 Hz, 1 H), 4.03 (AB, J$_{AB}$=8.1 Hz, 1 H), 4.24 (AB, J$_{AB}$=8.1 Hz, 1 H), 4.38 (dd, J=6.6 Hz, 10.1 Hz, 1 H), 4.75 (t, 1 H), 4.87 (d, J=9.0 Hz, 1 H), 5.55 (d, J=6.6 Hz, 1 H), 6.39 (s, 1 H), 7.37 (t, 2 H), 7.51 (t, 1 H), 8.02 (d, 2 H); IR (neat, cm$^{-1}$) 2958, 2356, 1771, 1732, 1716, 1699, 1652, 1558, 1456, 1393, 1268, 1169, 1107, 1070, 1026, 73,8. Anal. Calcd. for C$_{39}$H$_{54}$O$_{11}$Si: C, 64.44; H, 7.49. Found: C, 64.52, H, 7.49.

7-Triethylsilyl-10-crotonoyl-10-deacetylbaccatin III (IId)

White solid; [α]$_D^{22}$−68.57° © 7.00, CHCl$_3$); $^1$H NMR (CDCl$_3$, 250 MHz) δ 0.51 (q, 6 H), 0.86 (t, 9 H), 1.00 (s, 3 H), 1.20 (s, 3 H), 1.66 (s, 3 H), 1.80 (m, 1 H), 1.88 (d, 3 H), 2.19 (s, 2 H), 2.20 (s, 3 H), 2.26 (s, 3 H), 2.51 (m, 3 H), 3.87 (d, J=6.8 Hz, 1 H), 4.08 (AB, J$_{AB}$=8.2 Hz, 1 H), 4.26 (AB, J$_{AB}$=8.2 Hz, 1 H), 4.45 (dd, J=6.7 Hz, 9.9 Hz, 1 H), 4.80 (t, 1 H), 4.92 (d, J=9.7 Hz, 1 H), 5.61 (d, J=6.8 Hz, 1 H), 5.92 (d, J=15 Hz, 1 H), 6.48 (s, 1 H), 7.02 (m, 1 H), 7.42 (t, 2 H), 7.55 (t, 1 H), 8.07 (d, 2 H); $^{13}$C (CDCl$_3$, 63 MHz) δ 5.2, 6.7, 9.9, 14.9, 18.1, 20.1, 22.6, 26.7, 37.2, 38.2, 42.7, 47.3, 58.6, 67.9, 72.3, 74.7, 75.5, 76.5, 77.0, 77.5, 78.7, 80.8, 84.2, 122.3, 128.5, 129.4, 130.0, 132.7, 133.6, 143.9, 145.6, 164.7, 167.1, 170.7, 202.3; IR (neat, cm$^{-1}$) 2953, 2356, 1716, 1558, 1455, 1267, 1173, 1106, 1001, 822.

7-Triethylsilyl-10-N,N-dimethylcarbamoyl-10-deacetylbaccatin III (IIe)

White solid; [α]$_D^{21}$−30° © 2.00, CHCl$_3$); $^1$H NMR (CDCl$_3$, 300 MHz) δ 0.57 (m, 6 H), 0.91 (m, 9 H), 1.21 (s, 3 H), 1.27 (s, 3 H), 1.69 (s, 3 H), 1.84 (dt, 1 H), 2.21 (s, 2 H), 2.26 (s, 3 H), 2.29 (s, 2 H), 2.49 (m, 1 H), 2.95 (s, 3 H), 3.09 (s, 3 H), 3.91 (d, J=6.9 Hz, 1 H), 4.12 (AB, J$_{AB}$=8.4 Hz, 1 H), 4.30 (AB, J$_{AB}$=8.4 Hz, 1 H), 4.48 (dd, J=6.7 Hz, 10.2 Hz, 1 H), 4.84 (t, 1 H), 4.97 (d, J=9.0 Hz, 1 H), 5.64 (d, J=6.9 Hz, 1 H), 6.40 (s, 1 H), 7.46 (t, 2 H), 7.59 (t, 1 H), 8.11 (d, 2 H). HRMS (FAB, DCM/NBA/NaCl) m/z: Calcd. for C$_{38}$H55O$_{11}$NSiNa$^+$, 752,3442. Found, 752.3483.

7-Triethylsilyl-10-methoxycarbonyl-10-deacetylbaccatin III (IIf)

White solid; [α]$_D^{22}$−72.50° © 4.00, CHCl$_3$); $^1$H NMR (CDCl$_3$, 300 MHz) δ 0.54 (m, 6 H), 0.89 (m, 9 H), 1.03 (s, 3 H), 1.15 (s, 3 H), 1.67 (s, 3 H), 1.82 (dt, 1 H), 2.18 (s, 3 H), 2.25 (s, 2 H), 2.27 (s, 3 H), 2.47 (ddd, 1 H), 3.82 (s, 3 H), 3.84 (d, 1 H), 4.11 (AB, J$_{AB}$=8.1 Hz, 1 H), 4.27 (AB, J$_{AB}$=8.1 Hz, 1 H), 4.44 (dd, J=6.6 Hz, 10.2 Hz, 1 H), 4.83 (t, 1 H), 4.93 (d, J=9.0 Hz, 1 H), 5.59 (d, J=6.9 Hz, 1 H), 6.27 (s, 1 H), 7.43 (t, 2 H), 7.56 (t, 1 H), 8.07 (d, 2 H). IR (neat, cm$^{-1}$) 3524, 2957, 1715, 1442, 1371, 1266, 1108, 1025, 912, 820, 732.

7-Triethylsilyl-10-acryloyl-10-deacetylbaccatin III (IIg)

White solid; [α]$_D^{22}$−77.5° © 4.00, CHCl$_3$); $^1$H NMR (CDCl$_3$, 250 MHz) δ 0.51 (q, 6 H), 0.87 (t, 9 H), 1.01 (s, 3 H), 1.21 (s, 3 H), 1.68 (s, 3 H), 1.81 (m, 1 H), 2.15 (d, 2 H), 2.22 (s, 3 H), 2.27 (s, 3 H), 2.46 (m, 1 H), 3.87 (d, J=6.9 Hz, 1 H), 4.12 (AB, J$_{AB}$=8.3 Hz, 1 H), 4.28 (AB, J$_{AB}$=8.3 Hz, 1 H), 4.47 (dd, J=6.7 Hz, 10.2 Hz, 1 H), 4.81 (t, 1 H), 4.94 (d, J=8.7 Hz, 1 H),5.62 (d, J=6.9 Hz, 1 H), 5.88 (d, J=10.7 Hz, 1 H), 6.18 (m, 1 H), 6.47 (m, 1 H), 6.51 (s, 1 H), 7.02 (m, 1 H), 7.43 (t, 2 H), 7.56 (t, 1 H), 8.08 (d, 2 H); $^{13}$C NMR (CDCl$_3$, 63 MHz) δ 5.2, 6.7, 9.9, 14.9, 20.1, 22.6, 26.7, 37.2, 38.2, 42.7, 47.3, 58.6, 67.9, 72.3, 74.7, 75.8, 76.5, 77.0, 77.5,78.7, 80.8, 84.2, 128.1, 128.5, 129.3, 130.0, 131.5, 132.5, 133.6, 144.2, 164.5, 167.0, 170.7,202.0; IR (neat, cm$^{-1}$) 2950, 2250, 1734, 1717, 1653, 1635, 1506, 1457, 1362, 1269.

EXAMPLES 16–21

7-Triethylsilyl-10-O-substituted 2'-triisopropylsilyl-3'-(1-propenyl)docetaxel (I-P)

To a solution of 68 mg (0.097 mmol) of 7-triethylsilylbaccatin III (IIa) and 58 mg (0.15 mmol) of the N-$^t$BOC-β-lactam (VIa) in 4 mL of THF at −30° C. was added 0.12 mL (0.12 mmol) of LiHMDS. The mixture was allowed to warm to −10° C. and stirred for 1 hour and was then quenched with NH$_4$Cl. The aqueous layer was extracted with 75 mL of EtOAc and the combined organics were washed with NH$_4$Cl and brine. The organics were then dried over MgSO$_4$ and concentrated under vacuum. Upon purification by flash column chromatography on silica gel (hexane:EtOAc=4:1), 83 mg (79% yield) of pure protected taxoid 7-Triethylsilyl-10-acetyl-2'-triisopropylsilyl-3'-dephenyl-3'-(1-propenyl)docetaxel (1a-P) was collected (90% conversion, 88% conversion yield) as a white solid: Mp. 131.0–132.5° C.; $^1$H NMR (CDCl$_3$, 250 MHz) δ 0.57 (q, J=7.7 Hz, 6H), 0.92 (t, J=7.7 Hz, 9H), 1.05–1.11 (m, 21H), 1.20 (s, 3H), 1.23 (s, 3H), 1.32 (s, 9H), 1.69 (s, 3H), 1.73 (d, J=6.2 Hz, 3H), 1.76–1.95 (m, 1H), 2.01 (s, 3H), 2.18 (s, 3H), 2.22–2.35 (m, 2H), 2.41 (s, 3H), 2.43–2.60 (m, 1H), 3.83 (d, J=6.8 Hz, 1H), 4.17 (d, J=8.3 Hz, 1H), 4.31 (d, J=8.3 Hz, 1H), 4.42–4.55 (m, 2H), 4.62 (br m, 1H), 4.85–4.98 (m, 2H), 5.46 (dd, J=14.3, 6.2 Hz, 1H), 5.62–5.75 (m, 2H), 6.18 (t, J=9.1 Hz, 1H), 6.47 (s, 1H), 7.49 (t, J=7.2 Hz, 2H), 7.59 (t, J=7.2 Hz, 1H), 8.11 (d, J=7.2 Hz, 2H); $^{13}$C NMR (63 MHz, CDCl$_3$) δ5.29, 6.71, 10.04, 12.50, 14.41, 17.71, 17.94, 20.85, 21.24, 22.75, 26.39, 28.18, 35.36, 37.21, 43.28, 46.73, 55.0, 58.21, 71.23, 72.24, 74.89, 75.06, 78.05, 79.5, 81.12, 84.24, 127.67, 128.64, 129.25, 130.19, 133.40, 133.53, 140.74, 155.0, 167.0, 169.25, 169.89, 171.64, 203.72.

In a similar manner, the following 7-triethylsilyl-10-O-substituted 2'-triisopropylsilyl-3'-(1-propenyl)docetaxels (I-P) were obtained in high yields:

7-Triethylsilyl-10-propanoyl-2'-triisopropylsilyl-3'-dephenyl-3'-(2-methyl-1-propenyl)docetaxel (Ib-P)

$^1$H NMR (CDCl$_3$, 250 MHz) δ0.53 (q, 6 H), 0.86 (t, 9 H), 1.09 (s, 21 H), 1.15 (s, 3 H),1.19–1.20 (m, 6 H), 1.31 (s, 9 H), 1.66 (s, 3 H), 1.73 (s, 3 H), 1.77 (s, 3 H), 1.86 (m, 1 H), 1.19 (s,3 H), 2.34 (s, 3 H), 2.38 (s, 2 H), 2.41 (m, 1 H), 3.81 (d, J=6.6 Hz, 1 H), 4.15 (AB, J$_{AB}$=8.1 Hz, 1 H), 4.26 (AB, J$_{AB}$=8.1 Hz, 1 H), 4.41 (s, 1 H), 4.45 (m, 1 H), 4.79 (m, 1 H+NH), 4.89 (d, J=8.9 Hz, 1 H), 5.30 (d, J=7.7 Hz, 1 H), 5.65 (d, J=6.6 Hz, 1 H), 6.06 (t, 1 H), 6.47 (s, 1 H), 7.40 (t, 2 H), 7.54 (t, 1 H), 8.06 (d, 2 H).

7-Triethylsilyl-10-cyclopropanecarbonyl-2'-triisopropylsilyl-3'-dephenyl-3'-(2-methyl-1-propenyl) docetaxel (Ic-P)

$^1$H NMR (CDCl$_3$, 300 MHz) δ0.42 (m, 6 H), 0.82 (m, 9 H), 1.04 (s, 21 H), 1.12 (s, 3 H), 1.16 (s, 3 H), 1.18 (m, 2 H), 1.27 (s, 6 H), 1.62 (s, 3 H), 1.68 (bs, 5 H), 1.72 (s, 3 H), 1.84 (dt, 1 H), 1.94 (s, 3 H), 2.28 (s, 3 H), 2.32 (s,2 H), 2.88 (ddd, 1 H), 2.50 (d, 1 H), 3.76 (d, J=6.9 Hz, 1 H), 4.11 (AB, J$_{AB}$=8.4 Hz, 1 H), 4.22 (AB, J$_{AB}$=8.4 Hz, 1 H), 4.36 (bs, 1 H), 4.39 (m, 1 H), 4.69 (m, 1 H+NH), 4.85 (d, J=9.0 Hz, 1 H), 5.25 (d, J=8.1 Hz, 1 H), 5.61 (d, J=6.6 Hz, 1 H), 5.99 (t, 1 H), 6.41 (s, 1 H), 7.37 (t, 2 H), 7.51 (t, 1 H), 8.02 (d, 2 H).

7-Triethylsilyl-10crotonoyl-2'-triisopropylsilyl-3'-dephenyl-3'-(2-methyl-1-propenyl)docetaxel (Id-P)

$^1$H NMR (CDCl$_3$, 250 MHz) δ0.51 (q, 6 H), 0.87 (t, 9 H), 1.10 (s, 21 H), 1.17 (s, 3 H), 1.24 (s, 3 H), 1.32 (s, 9 H), 1.68 (s, 3 H), 1.74 (s, 3 H), 1.78 (s, 3 H), 1.86 (m, 1 H), 1.90 (d, 3 H), 2.03 (s, 3 H), 2.35 (s, 3 H), 2.39 (s, 2 H), 2.45 (m, 1 H), 3.84 (d, J=7.1 Hz, 1 H), 4.17 (AB, J$_{AB}$=8.3 Hz, 1 H), 4.28 (AB, J$_{AB}$=8.3 Hz, 1 H), 4.42 (d, 1 H), 4.45 (dd, J=6.4 Hz, 10.2 Hz, 1 H), 4.75 (m, 1 H+NH), 4.91 (d, J=8.5 Hz, 1 H), 5.31 (d, J=8.2 Hz, 1 H), 5.67 (d, J=7.1 Hz, 1 H), 5.92 (d, 1 H), 6.04 (t, 1 H), 6.51 (s, 1 H), 6.99 (m, 1 H), 7.42 (t, 2 H), 7.56 (t, 1 H), 8.08 (d, 2 H).

7-Triethylsilyl-10-N,N-dimethylcarbamoyl-2'-triisopropylsilyl-3'-dephenyl-3'-(2-methyl-1-propenyl)docetaxel (Ie-P)

$^1$H NMR (CDCl$_3$, 250 MHz) δ0.52 (m, 6 H), 0.86 (m, 9 H), 1.09 (s, 21 H), 1.17 (s, 3 H), 1.19 (s, 3 H), 1.31 (s, 6 H), 1.66 (s, 3 H), 1.72 (s, 3 H), 1.76 (s, 3 H), 1.85 (dt, 1 H), 2.03 (s, 3 H), 2.33 (s, 3 H), 2.38 (s, 3 H), 2.48 (ddd, 1 H), 2.91 (s, 3 H), 3.03 (s, 3 H), 3.82 (s, J=6.9 Hz, 1 H), 4.15 (AB, J$_{AB}$=8.2 Hz, 1 H), 4.25 (AB, J$_{AB}$=8.2 Hz, 1 H), 4.39 (m, 1 H), 4.41 (bs, 1 H), 4.73 (m, 1 H+NH), 4.89 (d, J=8.8 Hz, 1 H), 5.30 (d, J=8.0 Hz, 1 H), 5.65 (d, J=6.9 Hz, 1 H), 6.04 (t, 1 H), 6.38 (s, 1 H), 7.39 (t, 2 H), 7.54 (t, 1 H), 8.06 (d, 2 H).

7-Triethylsilyl-10methoxycarbonyl-2'-triisopropylsilyl-3'-dephenyl-3'-(2-methyl-1-propenyl) docetaxel (If-P)

$^1$H NMR(CDCl$_3$, 250 MHz) δ0.52 (m, 6 H), 0.88 (m, 9 H), 1.10 (s, 21 H), 1.18 (s, 6 H), 1.32 (s, 9 H), 1.68 (s, 3 H), 1.73 (s, 3 H), 1.77 (s, 3 H), 1.83 (dt, 1 H), 2.00 (s, 3 H), 2.34 (s, 3 H), 2.38 (s, 2 H), 2.44 (ddd, 1 H), 3.79 (d, 1 H), 3.80 (s, 3 H), 4.15 (AB, J$_{AB}$=8.3 Hz, 1 H), 4.27 (AB, J$_{AB}$=8.3 Hz, 1 H), 4.41 (d, J=2.3 Hz, 1 H), 4.44 (m, 1 H), 4.74 (m, 1 H+NH), 4.90 (d, J=8.3 Hz, 1 H), 5.30 (d, J=8.2 Hz, 1 H), 5.64 (d, J=7.0Hz, 1 H), 6.04 (t, 1 H), 6.26 (s, 1 H), 7.40 (t, 2 H), 7.55 (t, 1 H), 8.06 (d, 2 H).

7-Triethylsilyl-10-acryloyl-2'-triisopropylsilyl-3'-dephenyl-3'-(2-methyl-1-propenyl)docetaxel (Ig-P)

$^1$H NMR (CDCl$_3$, 250 MHz) δ0.51 (m, 6 H), 0.86 (m, 9 H), 1.10 (s, 21 H), 1.16 (s, 3 H), 1.24 (s, 3 H), 1.32 (s, 9 H), 1.62 (s, 3 H), 1.68 (s, 3 H), 1.74 (s, 3 H), 1.78 (s, 3 H), 1.83 (m, 1 H), 2.35 (s, 2 H), 2.39 (s, 3 H), 2.42 (m, 1 H), 3.83 (d, J=7.3 Hz, 1 H), 4.16 (AB, J$_{AB}$=8.3 Hz, 1 H), 4.28 (AB, J$_{AB}$=8.3 Hz, 1 H), 4.41 (d, J=2.1 Hz, 1 H), 4.45 (m, 1 H), 4.74 (m, 1 H+NH), 4.90 (d, J=9.4Hz, 1 H), 5.30 (d, J=7.8 Hz, 1 H), 5.62 (d, J=7.3 Hz, 1 H), 5.88 (d, J=10.3 Hz, 1 H), 6.04 (t, 1 H), 6.17 (m, 1 H), 6.46 (m, 1 H), 6.52 (s, 1 H), 7.41 (t, 2 H), 7.56 (t, 1 H), 8.07 (d, 2 H).

EXAMPLES 22–28

3'-Dephenyl-3'-(1-alkenyl)-10-O-substituted docetaxel (I)

To a solution of 46 mg. (0.042 mmol) of the protected taxoid Ia-P in 3 mL of 1:1 mixture of acetonitrile and pyridine was added 0.5 mL of HF/pyridine (70:30). The reaction mixture was stirred at 35–40° C. for 2 hours. The reaction was quenched with 2N HCl. The mixture was extracted with EtOAc and the organic layer washed with 2N HCl and brine. After drying over MgSO$_4$, the crude product was purified by flash chromatography on silica gel (hexane:EtOAc=1:2) to yield 24 mg (70% yield) of the pure taxoid 3'-dephenyl-3'-(1-propenyl)-10-acetyldocetaxel (Ia) as a white solid: Mp. 152.0–155.0° C.; [α]$_D$ –86.7° (c, 0.15, CHCl$_3$); $^1$H NMR (CDCl$_3$, 250 MHz) δ1.15 (s, 3H), 1.25 (s, 3H), 1.32 (s, 9H), 1.67 (s, 3H), 1.75 (d, J=6.3 Hz, 3H), 1.86 (br s, 4H), 2.23 (s, 3H), 2.30–2.39 (m, 2H), 2.40 (s, 3H), 2.45–2.60 (m, 1H), 3.38 (br s, 1H), 3.81 (d, J=6.9 Hz, 1H), 4.17 (d, J=8.4 Hz, 1H), 4.30–4.33 (m, 2H), 4.42 (dd, J=10.5, 6.9 Hz, 1H), 4.60 (br m, 1H), 4.90–4.98 (m, 2H), 5.53 (dd, J=16.2, 6.3 Hz, 1H), 5.67 (d, J=6.9 Hz, 1H), 5.72–5.82 (m, 1H), 6.21 (t, J=8.8 Hz, 1H), 6.30 (s, 1H), 7.52 (t, J=7.2 Hz, 2H), 7.61 (t, J=7.2 Hz, 1H), 8.11 (d, J=7.1 Hz, 2H); $^{13}$C NMR (63 MHz, CDCl$_3$) δ9.53, 14.95, 17.87, 20.84, 21.82, 22.54, 26.69, 28.18, 35.45, 35.60, 54.90, 58.62, 72.19, 73.12, 74.98, 75.61, 79.03, 79.55, 81.10, 84.41, 127.37, 128.71, 129.1, 130.19, 133.1, 133.68, 142.50, 155.50, 167.20, 170.13, 171.5, 173.40, 203.73. Anal. Calcd. for C$_{42}$H$_{55}$O$_{15}$N: C, 61.98; H, 6.81; N, 1.72. Found: C, 62.12; H, 6.59; N, 1.67.

In a similar manner, the following 3'-dephenyl-3'-(1-alkenyl)-10-O-substituted docetaxels (Ib-g) were obtained in high yields:

3'-Dephenyl-3'-(2-methyl-1-propenyl)-10-propanoyldocetaxel (Ib)

White solid; $[\alpha]_D^{21}$ –40° © 1.00, CHCl$_3$); $^1$H NMR (CDCl$_3$, 300 MHz) δ1.08 (s, 3 H), 1.13–1.18 (m, 6 H), 1.28 (s, 9 H), 1.60 (s, 3 H), 1.69 (s, 6 H), 1.72 (m, 1 H), 1.83 (s, 3 H), 2.29 (s, 3 H), 2.31 (s, 2 H), 2.44 (m, 3 H), 3.38 (bs, OH), 3.74 (d, J=6.9 Hz, 1 H), 4.10 (AB, J$_{AB}$=8.1 Hz, 1 H), 4.13 (bs, 1 H), 4.22 (AB, J$_{AB}$=8.1 Hz, 1 H), 4.33 (dd, J=7.5 Hz, 10.1 Hz, 1 H), 4.67 (m, 1 H+NH), 4.88 (d, J=9.3 Hz, 1 H), 5.23 (d, J=8.4 Hz, 1 H), 5.59 (d, J=6.9 Hz, 1 H), 6.06 (t, 1 H), 6.24 (s, 1 H), 7.37 (t, 2 H), 7.51 (t, 1 H), 8.01 (d, 2 H); $^{13}$C NMR (CDCl$_3$, 63 MHz), δ 9.0, 9.5, 14.9, 18.5, 21.8, 22.3, 25.7, 26.6, 27.5, 28.2, 35.5, 43.1, 45.6, 51.6, 55.5, 58.5, 72.1, 72.3, 73.7, 75.0, 75.4, 76.4, 76.5, 77.0, 77.5, 79.1, 79.9, 81.0, 84.3, 120.6, 128.6, 129.2, 130.1, 132.9, 133.6, 137.8, 142.4, 155.4, 166.9, 170.1, 173.0, 174.6, 203.8. HRMS (FAB, DCM/NBA), m/z: Calcd. for C$_{44}$H$_{59}$O$_{15}$NH$^+$, 842.3962. Found, 842.4007.

3'-Dephenyl-3'-(2-methyl-1-propenyl)-10-cyclopropanecarbonyldocetaxel (Ic)

White solid; $[\alpha]_D^{21}$ –160° © 1.00, CHCl$_3$); $^1$H NMR (CDCl$_3$, 250 MHz) δ1.10 (m, 2 H), 1.14 (s, 3 H), 1.25 (s, 3 H), 1.34 (s, 9 H), 1.65 (s, 3 H), 1.71 (s, 2 H), 1.75 (s, 6 H), 1.84 (dt, 1 H), 1.88 (s, 3 H), 2.34 (s, 3 H), 2.37 (s, 2 H), 2.46 (ddd, 1 H), 2.56 (d, J=3.3 Hz, 1 H), 3.36 (d, OH), 3.78 (d, J=6.9 Hz, 1 H), 4.13 (d, J=8.4 Hz, 1 H), 4.18 (bs, 1 H), 4.27 (AB, J$_{AB}$=8.4 Hz, 1 H), 4.40 (m, 1 H), 4.72 (m, 1 H+NH), 4.93 (AB, J$_{AB}$=8.6 Hz, 1 H), 5.28 (d, J=7.6 Hz, 1 H), 5.64 (d, J=6.9 Hz, 1 H), 6.16 (t, 1 H), 6.28 (s, 1 H), 7.43 (t, 2 H), 7.56 (t, 1 H), 8.07 (d, 2 H); $^{13}$C NMR (CDCl$_3$, 63 MHz) δ 9.1, 9.4, 9.5, 13.0, 14.9, 18.5, 21.9, 22.4, 25.7, 26.7, 28.2, 35.5, 35.6, 43.2, 45.6, 51.6, 58.5, 72.2, 72.3, 73.7, 75.0, 75.4, 76.5, 77.0, 77.5, 79.2, 79.7, 81.0, 84.4, 120.6, 128.6, 129.2, 130.1, 132.9, 133.6, 137.9, 142.6, 155.4, 166.9, 170.1, 175.1, 203.9; IR (neat, cm$^{-1}$): 3368, 2989, 2915, 1786, 1754, 1725, 1709, 1641, 1630, 1355, 1315, 1109. HRMS (FAB, DCM/NBA/NaCl), m/z: Calcd. for C$_{45}$H$_{59}$O$_{15}$NNa$^+$, 876.3784. Found 876.3782.

3'-Dephenyl-3'-(2-methyl-1-propenyl)-10-crotonoyldocetaxel (Id)

White solid; $[\alpha]_D^{21}$ –30° © 1.00, CHCl$_3$); $^1$H NMR (CDCl$_3$, 250 MHz) δ 1.16 (s, 3 H), 1.26 (s, 3 H), 1.35 (s, 9 H), 1.67 (s, 3 H), 1.76 (s, 6 H), 1.22 (m, 1 H), 1.90 (s, 3 H), 1.92 (dd, 3 H), 2.35 (s, 3 H), 2.39 (s, 2 H), 2.49 (m, 1 H), 3.38 (bs, OH), 3.82 (d, J=6.9 Hz, 1 H), 4.10 (AB, J$_{AB}$=8.3 Hz, 1 H), 4.20 (bs, 1 H), 4.29 (AB, J$_{AB}$=8.3 Hz, 1 H), 4.45 (m, 1 H), 4.73 (m, 1 H+NH), 4.95 (d, J=7.9 Hz, 1 H), 5.30 (d, 1 H), 5.66 (d, J=6.9 Hz, 1 H), 5.95 (dd, 1 H), 6.14 (t, 1 H), 6.36 (s, 1 H), 7.03 (m, 1 H), 7.44 (t, 2 H), 7.57 (t, 1 H), 8.08 (d, 2 H); $^{13}$C NMR (CDCl$_3$, 63 MHz) δ 9.5, 14.9, 18.2, 18.5, 21.9, 22.4, 25.7, 26.7, 28.2, 29.6, 35.5, 35.6, 43.2, 45.6, 51.6, 58.6, 72.2, 72.3, 73.7, 75.1, 75.3, 76.5, 77.0, 77.5, 79.2, 79.9, 81.0, 84.4, 120.6, 121.6, 128.6, 129.2, 130.1, 132.9, 133.6, 137.9, 142.6, 147.2, 155.4, 166.2, 166.9, 170.0, 173.0, 174.6, 203.8. HRMS (FAB, DCN/NBA/NaCl) m/z: Calcd. for C$_{45}$H$_{59}$O$_{15}$NNa$^+$, 876.3782. Found, 876.3749.

3'-Dephenyl-3'-(2-methyl-1-propenyl)-10-N,N-dimethylcarbamoyldocetaxel (Ie)

White solid; $[\alpha]_D^{21}$ –50 ° © 2.00, CHCl$_3$); $^1$H NMR (CDCl$_3$, 250 MHz) δ 1.13 (s, 3 H), 1.23 (s, 3 H), 1.33 (s, 9 H), 1.64 (s, 3 H), 1.74 (s, 6 H), 1.85 (dt, 1 H), 1.89 (s, 3 H), 2.33 (s, 3 H), 2.36 (s, 2 H), 2.45 (ddd, 1 H), 2.93 (s, 3 H), 3.02 (s, 3 H), 3.20 (bs, OH), 3.45 (d, OH), 3.78 (d, J=6.9 Hz, 1 H), 4.14 (AB, J$_{AB}$=8.4 Hz, 1 H), 4.18 (bs, 1 H), 4.26 (AB, J$_{AB}$=8.4 Hz, 1 H), 4.40 (dd, J=6.7 Hz, 10.2 Hz, 1 H), 4.69 (d, 1 H), 4.80 (s, NH), 4.93 (d, J=8.6 Hz, 1 H), 5.27 (d, J=7.6 Hz, 1 H), 5.62 (d, J=6.9 Hz, 1 H), 6.12 (t, 1 H), 6.23 (s, 1 H), 7.41 (t, 2 H), 7.55 (t, 1 H), 8.06 (d, 2 H); $^{13}$C NMR (CDCl$_3$, 63 MHz) δ 9.3, 15.0, 18.5, 22.2, 22.3, 25.7, 26.8, 28.2, 35.3, 35.6, 36.0, 36.6, 43.1, 45.6, 51.6, 58.4, 72.3, 72.4, 73.7, 75.2, 76.2, 76.4, 76.5, 77.0, 77.5, 79.2, 81.0, 84.6, 128.6, 129.2, 130.1, 133.1, 133.6, 137.8, 142.9, 155.4, 156.1, 166.9, 170.0, 173.0, 205.6. HRMS (FAB, DCM/NBA) m/z: Calcd. for C$_{44}$H$_{60}$O$_{15}$N$_2$Na$^+$, 879.3891. Found, 879.3870.

3'-Dephenyl-3'-(2-methyl-1-propenyl)-10-methoxycarbonyldocetaxel (If)

White solid; $[\alpha]_D^{21}$ –15.0° © 2.00, CHCl$_3$); $^1$H NMR (CDCl$_3$, 250 MHz) δ1.14 (s, 3 H), 1.23 (s, 3 H), 1.33 (s, 9 H), 1.68 (s, 3 H), 1.71 (s, 6 H), 1.87 (m, 1 H), 1.92 (s, 3 H), 2.34 (s, 3 H), 2.47 (d, 2 H), 2.55 (m, 1 H), 3.40 (bs, OH), 3.76 (d, J=6.9 Hz, 1 H), 3.85 (s, 3 H), 4.15 (AB, J$_{AB}$=8.3 Hz, 1 H), 4.19 (bs, 1 H), 4.28 (AB, J$_{AB}$=8.3 Hz, 1 H), 4.38 (m, 1 H), 4.72 (m, 1 H+NH), 4.93 (d, J=8.6 Hz, 1 H), 5.29 (d, J=7.8 Hz, 1 H), 5.64 (d, J=6.9 Hz, 1 H), 6.11 (s, 1 H), 6.15 (s, 1 H), 7.43 (t, 2 H), 7.56 (t, 1 H), 8.07 (d, 2 H); $^{13}$C NMR (CDCl$_3$, 75 MHz) δ 9.4, 15.0, 18.5, 21.7, 22.3, 25.7, 26.5, 28.2, 35.5, 43.1, 45.6, 51.6, 55.5, 58.6, 72.0, 72.2, 73.7, 75.0, 76.4, 76.5, 77.0, 77.2, 77.4, 78.3, 79.1, 79.9, 81.0, 84.3, 120.6, 128.6, 129.2, 130.1, 132.5, 133.6, 137.9, 143.4, 155.4, 155.7, 166.9, 170.1, 172.9, 203.9. HRMS (FAB, DCM/NBA/PPG) m/z: Calcd. for C$_{43}$H$_{57}$O$_{16}$NH$^+$, 844.3710. Found, 844.3755.

3'-Dephenyl-3'-trifluoromethyl-10-acetyldocetaxel (Ig)

White solid; $^1$H NMR (250 MHz CDCl$_3$): δ 1.14 (s, 3 H), 1.24 (s, 3 H), 1.30 (s, 9 H), 1.67 (s, 3 H), 1.75 (br s, 1 H), 1.92 (s, 3 H), 2.24 (s, 3 H), 2.28–2.37 (m, 5 H), 2.48–2.61 (m, 1 H), 3.46 (br d, 1 H), 3.79 (d, J=7.0 Hz, 1 H), 4.16 (d, J=8.3 Hz, 1 H), 4.30 (d, J=8.3 Hz, 1 H), 4.39 (br t, 1 H), 4.71–4.84 (m, 2 H), 4.93 (d, J=8.1 Hz, 1 H), 5.24 (d, J=10.6 Hz, 1 H), 5.65 (d, J=7.0 Hz, 1 H), 6.21–6.28 (m, 2 H), 7.49 (t, J=7.4 Hz, 2 H), 7.61 (t, J=7.4 Hz, 1 H), 8.11 (d, J=7.4 Hz, 2 H), $^{13}$C NMR (63 MHz, CDCl$_3$) δ 9.57, 14.82, 20.86, 21.92, 22.35, 26.72, 27.94, 35.39, 35.58, 43.25, 45.65, 53.54, 54.03, 58.59, 68.08, 73.15, 73.32, 74.94, 75.48, 76.51, 79.01, 81.18, 81.37, 84.43, 126.24, 128.77, 129.01, 130.23, 133.38, 133.74, 141.60, 154.67, 167.16, 170.28, 171.25, 171.76, 203.54. Anal. Calc. for C$_{40}$H$_{50}$F$_3$NO$_{15}$:C, 57.07; H, 5.99; N, 1.66. Found: C, 56:33; H, 6.02; N, 1.69.

EXAMPLES 29–32

3'-Dephenyl-3'-(2-methylpropyl)-10-O-substituted docetaxel (Ib')

A solution of 14 mg (0.016 mmol) of Ib in 2.0 mL of ethyl acetate was stirred under one atmosphere of hydrogen at room temperature, in the presence of palladium (10%) on activated carbon (23 mg). After 24 hours, the suspension was purified by chromatography on silica gel (EtOAc) to afford 14 mg (100%) of 3'-dephenyl-3'-(2-methylpropyl)-10-propanoyldocetaxel (Ib') as a white solid: $[\alpha]_D^{21}$ –30° © 1.00, CHCl$_3$); $^1$H NMR (CDCl$_3$, 250 MHz) δ0.96 (d, 6 H), 1.13 (s, 3 H), 1.22–1.27 (m, 6 H), 1.30 (s, 9 H), 1.63 (s, 3 H), 1.73 (s, 2 H), 1.82 (m, 1 H), 1.88 (s, 3 H), 2.36 (s, 3 H), 2.40 (s, 2 H), 2.46 (m, 1 H), 2.49 (m, 2 H), 3.25 (bs, OH), 3.79 (d, J=7.0 Hz, 1 H), 4.09 (AB, J$_{AB}$=8.3 Hz, 1 H), 4.16 (bs, 1 H), 4.27 (AB, J$_{AB}$=8.3 Hz, 1 H), 4.38 (dd, J=6.7 Hz, 10.2 Hz, 1 H), 4.57 (d, J=9.5 Hz, NH), 4.94 (d, J=8.0 Hz, 1 H), 5.64 (d, J=7.0 Hz, 1 H), 6.13 (t, 1 H), 6.30 (s, 1 H), 7.43 (t, 2 H), 7.56 (t, 1 H), 8.08 (d, 2 H); $^{13}$C NMR (CDCl$_3$, 63 MHz) δ 9.0, 9.5, 14.9, 21.8, 21.9, 22.5, 23.2, 24.6, 26.5, 27.5, 28.1, 29.6, 35.5, 41.2, 43.1, 45.6, 51.3, 58.5, 72.1, 72.6, 73.0, 75.1, 75.4, 76.4, 76.5, 77.0, 77.5, 79.1, 79.7, 81.0, 84.4, 128.6, 129.2, 130.1, 132.9, 133.6, 142.4, 155.5, 166.9, 169.9, 173.9, 174.6, 203.8. HRMS (FAB, DCM/NBA) m/z: Calcd. for C$_{44}$H$_{61}$O$_{15}$NH$^+$, 844.4119. Found, 844.4157.

In the same manner, the following 3'-dephenyl-3'-(2-methylpropyl)-10-O-substituted docetaxels (Ic'-f') were obtained in quantitative yields:

3'-Dephenyl-3'-(2-methylpropyl)-10-cyclopropanecarbonyldocetaxel (Ic')

White solid; [α]$_D^{21}$–30° © 1.00, CHCl$_3$); $^1$H NMR (CDCl$_3$, 250 MHz) δ 0.96 (d, 6 H), 1.09 (m, 2 H), 1.14 (s, 3 H), 1.24 (s, 3 H), 1.30 (s, 9 H), 1.62–1.70 (m, 4 H), 1.66 (s, 3 H), 1.73 (m, 1 H), 1.88 (s, 3 H), 2.36 (s, 3 H), 2.39 (s, 1 H), 2.48 (ddd, 1 H), 2.50 (d, 1 H), 3.20 (d, OH), 3.78 (d, J=6.9 Hz, 1 H), 4.16 (AB, J$_{AB}$=8.3 Hz, 1 H), 4.20 (bs, 1 H), 4.27 (AB, J$_{AB}$=8.3 Hz, 1 H), 4.40 (m, 1 H), 4.55 (d, NH), 4.93 (d, J=8.1 Hz, 1 H), 5.64 (d, J=7.0 Hz, 1 H), 6.14 (t, 1 H), 6.29 (s, 1 H), 7.43 (t, 2 H), 7.56 (t, 1 H), 8.09 (d, 2 H); $^{13}$C NMR (CDCl$_3$, 63 MHz) δ 9.1, 9.4, 9.5, 13.0, 14.9, 21.9, 22.0, 22.5, 23.2, 24.7, 26.6, 28.1, 35.4, 35.5, 41.2, 43.1, 45.6, 51.3, 58.5, 72.2, 72.7, 72.9, 75.1, 75.4, 76.5, 77.0, 77.5, 79.2, 79.7, 81.0, 84.4, 128.6, 129.2, 130.2, 132.9, 133.6, 142.6, 155.5, 166.9, 169.9, 173.9, 175.1, 203.9. HRMS (FAB, DCM/NBC/NaCl), m/z: Calcd. for C$_{45}$H$_{61}$O$_{15}$NNa$^+$, 878.3938. Found, 878.3926.

3'-Dephenyl-3'-(2-methylpropyl)-10-N,N-dimethylcarbamoyldocetaxel (Ie')

White solid; [α]$_D^{21}$–80° ©2.00, CHCl$_3$); $^1$H NMR (CDCl$_3$, 250 MHz) δ 0.95 (d, 6 H), 1.14 (s, 3 H), 1.23 (s, 3 H), 1.29 (s, 9 H), 1.66 (s, 3 H), 1.68 (m, 2 H), 1.82 (m, 1 H), 1.90 (s, 3 H), 2.36 (s, 3 H), 2.39 (s, 2 H), 2.50 (m, 1 H), 2.95 (s, 3 H), 3.03 (s, 3 H), 3.22 (d, OH), 3.78 (d, J=7.0 Hz, 1 H), 4.10 (AB, J$_{AB}$=8.3 Hz, 1 H), 4.16 (bs, 1 H), 4.27 (AB, J$_{AB}$=8.3 Hz, 1 H), 4.41 (dd, J=6.5 Hz, 10.2 Hz, 1 H), 4.56 (d, NH), 4.95 (d, J=8.1 Hz, 1 H), 5.63 (d, J=7.0 Hz, 1 H), 6.14 (t, 1 H), 6.24 (s, 1 H), 7.42 (t, 2 H), 7.56 (t, 1 H), 8.08 (d, 2 H); $^{13}$C NMR (CDCl$_3$, 75 MHz) δ 9.8, 15.3, 22.3, 22.7, 22.9, 23.6, 25.1, 27.2, 28.5, 35.8, 36.0, 36.4, 37.0, 41.6, 43.6, 46.0, 51.7, 58.9, 72.8, 73.1, 75.7, 76.6, 76.8, 76.9, 77.1, 77.4, 77.6, 77.8, 79.6, 80.0, 81.5, 85.0, 128.7, 129.0, 129.7, 130.6, 133.6, 133.9, 143.3, 155.9, 156.5, 167.3, 170.3, 174.3, 206.0. HRMS (FAB) m/z: Calcd. for C$_{44}$H$_{62}$O$_{15}$N$_2$Na$^+$, 881.4074. Found, 881.4047.

3'-Dephenyl-3'-(2-methylpropyl)-10-methoxycarbonyldocetaxel (If')

White solid; [α]$_D^{21}$–70° © 1.00, CHCl$_3$); $^1$H NMR (CDCl$_3$, 250 MHz) δ 0.96 (d, 6 H), 1.14 (s, 3 H), 1.23 (s, 3 H), 1.30 (s, 9 H), 1.66 (s, 2 H), 1.69 (s, 3 H), 1.84 (m, 1 H), 1.92 (s, 3 H), 2.37 (s, 3 H), 2.47 (s, 2 H), 2.55 (m, 1 H), 3.24 (d, OH), 3.77 (d, J=6.8 Hz, 1 H), 3.86 (s, 3 ), 4.16 (AB, J$_{AB}$=8.2 Hz, 1 H), 4.17 (bs, 1 H), 4.28 (AB, J$_{AB}$=8.2 Hz, 1 H), 4.40 (dd, 1 H), 4.56 (d, J=9.3 Hz, NH), 4.94 (d, J=8.0 Hz, 1 H), 5.65 (d, J=7.0 Hz, 1 H), 6.11 (s, 1 H), 6.18 (t, 1 H), 7.43 (t, 2 H), 7.56 (t, 1 H), 8.09 (d, 2 H); $^{13}$C NMR (CDCl$_3$, 75 MHz) δ 9.5, 15.0, 21.8, 22.5, 23.2, 24.7, 26.5, 28.1, 35.5, 35.6, 41.2, 43.0, 45.5, 51.3, 55.5, 58.5, 72.0, 72.6, 73.0, 75.0, 76.5, 77.0, 77.5, 78.3, 79.1, 79.7, 81.0, 84.3, 128.6, 129.2, 130.2, 132.5, 133.6, 143.5, 155.5, 155.7, 166.9, 170.0, 173.9, 204.0. HRMS (FAB, DCM/NBA) m/z: Calcd. for C$_{43}$H$_{59}$O$_{16}$NH$^+$, 846.3912. Found, 846.3942.

EXAMPLE 33

Taxoids Ia and Ig were evaluated for tumor growth inhibitory activities against human tumor cell line, A121 (ovarian carcinoma), A549 (non-small cell lung carcinoma), HT-29 (colon carcinoma), MCF7 (mammary carcinoma) or MCF7-R (mammary carcinoma cells 180-fold resistant to adriamycin), after 72 h drug exposure according to the literature method (see below). Results are shown in Table 1. Lower numbers indicate higher potency. Paclitaxel, docetaxel, and RAH-1 (see above) were also used for comparison. The data represent the mean values of at least three separate experiments. Lower numbers indicate greater activity.

TABLE 1

| Taxoid | A121[a] (ovarian) | A549[a] (NSCLC) | HT-29[a] (colon) | MCF7[a] (breast) | MCF7-R[a] |
|---|---|---|---|---|---|
| Paclitaxel | 6.1 | 3.6 | 3.2 | 1.7 | 300 |
| Docetaxel | 1.2 | 1.0 | 1.2 | 1.0 | 235 |
| RAH-1 | 1.4 | 0.45 | 0.96 | 0.54 | 113 |
| Ia | 0.90 | 0.54 | 0.76 | 0.51 | 14 |
| Ig | 0.37 | 0.25 | 0.4 | 0.25 | 17 |

[a]The concentration of compound which inhibits 50% (IC$_{50}$, nM) of the growth of human tumor cell line.

Assessment of cell growth inhibition was determined according to the methods of Skehan et al., *J. Nat. Cancer Inst.* 1990, 82, 1107. Briefly, cells were plated between 400 and 1200 cells/well in 96 well plates and incubated at 37° C. for 15–18 h prior to drug addition to allow attachment of cells. Compounds tested were solubilized in 100% DMSO and further diluted in RPMI-1640 containing 10 mM HEPES. Each cell line was treated with 10 concentrations of compounds (5 log range). After a 72 h incubation, 100 mL of ice-cold 50% TCA was added to each well and incubated for 1 h at 4° C. Plates were then washed 5 times with tap water to remove TCA, low-molecular-weight metabolites and serum proteins. Sulforhodamine B (SRB) (0.4%, 50 mL) was added to each well. Following a 5 min incubation atroom temperature, plates were rinsed 5 times with 0.1% acetic acid and air dried. Bound dye was solubilized with 10 mM Tris Base (pH 10.5) for 5 min on a gyratory shaker. Optical density was measured at 570 nm.

Data were fit with the Sigmoid-Emax concentration-effect model (see Holford, N. H. G.; Scheiner, L. B., "Understanding the dose-effect relationship: Clinical applications of pharmaco-kinetic-pharmacodynamic models.", *Clin. Pharmacokin.* 1981, 6, 429–453) with non-linear regression, weighted by the reciprocal of the square of the predicted response. The fitting software was developed by the Roswell Park Cancer Institute with Microsoft FORTRAN, and uses the Marquardt algorithm (see Marquardt, D. W., "An algorithm for least squares estimation of nonlinear parameters", *J. Soc. Ind. Appl. Math.* 1963, 11, 431–441) as adopted by Nash (see Nash, J. C., "Compact numerical method for computers: Linear algebra and function minimization", John Wiley & Sons, New York, 1979) for the non-linear regression. The concentration of drug which resulted in 50% growth inhibition (IC$_{50}$) was calculated.

Since the new taxoids of this invention are unique in that these taxoids possess extremely high activities against drug-resistant human breast cancer cells MCF7-R (two orders of magnitude better than paclitaxel and docetaxel), the activities of these taxoids other than Ia and Ig were evaluated against human breast cancer cells (MCF7) (sensitive) and resistant cells (MCF7-R) (resistant) in the same manner as described above. Results are summarized in TABLE 2.

TABLE 2

| Taxoid | $R^1$ | $R^5$ | MCF7 $IC_{50}$ (nM) | MCF7-R $IC_{50}$ (nM) |
|---|---|---|---|---|
| Ib  | 2-methyl-1-propenyl | $COCH_2CH_3$ | 0.21 | 2.16 |
| Ib' | 2-methylpropyl | $COCH_2CH_3$ | 0.35 | 2.84 |
| Ic  | 2-methyl-1-propenyl | cyclopropylcarbonyl | 0.20 | 2.11 |
| Ic' | 2-methylpropyl | cyclopropylcarbonyl | 0.51 | 4.33 |
| Id  | 2-methyl-1-propenyl | crotonoyl | 0.26 | 3.35 |
| Ie  | 2-methyl-1-propenyl | $CON(CH_3)_2$ | 0.13 | 4.91 |
| Ie' | 2-methylpropyl | $CON(CH_3)_2$ | 0.36 | 5.80 |
| If  | 2-methyl-1-propenyl | $CO_2CH_3$ | 0.14 | 5.25 |
| If' | 2-methylpropyl | $CO_2CH_3$ | 0.48 | 6.35 |

Extensive studies have been performed in different laboratories on the structure-activity relationships of paclitaxel and their congeners, taxoids. (Guénard, D., et al. *Acc. Chem. Res.* 1993, 26, 160–167; Georg, G. I., et al. in Taxol®: *Science and Applications*; M. Suffness. Ed.: CRC Press: New York, 1995, pp 317–375) As a part of our continuing structure-activity relationship study of taxoids (Ojima, I., et al. *Curr. Med. Chem*, 1999, 6, 927–954; Ojima. I., et al., in *Adv. Med. Chem.*; B. E. Maryanoff and A. B. Reitz, Ed.; JAI Press: Greenwich, Conn. 1998: Vol. 4; pp 69–124), we have demonstrated that appropriate modification at the C-10 position and replacement of the phenyl group with an alkenyl or alkyl group at the C-3' position of taxoids provide second generation taxoids which exhibit 1–2 orders of magnitude higher potency against drug-resistant cancer cells lines (Ojima I. et al., *J. Med. Chem.* 1996, 39, 3889–3896; Ojima. I., et al., *J. Org. Chem.* 1998, 63, 224–225). Modifications at the 3-position of the C-2 benzoate with certain substituents (e.g., CN, $N_3$, MeO, and Cl) have been shown to improve anticancer activity against the P-388 cell line. Kingston, D. G. I., in *Taxane Anticancer, Agents: Basic Science and Current Status; ACS. Symp. Ser.* 583, Georg, G. I., et al., eds., pp 203–216 (American Chemical Society: Washington, D.C., 1995). Chaudhary, A. G., et al., *J. Am. Chem. Soc.* 1994. 116, 4097–4098. Kingston, D. G. L., et al., *J. Med. Chem.* 1998, 41, 3715–3726.

We report here the syntheses and structure-activity relationships of new second-generation taxoids having a combination of these two modifications and providing a series of highly active antitumor taxoids.

EXAMPLE 34

As shown in Scheme 1 below, 10-deacetylbaccatin III (10-DAB, 1) (Marder-Karsenti, R., et al., *J. Org. Chem.* 1997, 62, 6631–6637) was first reacted with chlorotriethylsilane (TESCl) and imidazole in DMF to give 7,10,13-tri-TES-DAB 2 in 96% yield. Removal of the 2-benzoyl group of baccatin 2 with Red-Al® afforded diol 3 in 97% yield. Esterification of 3 with appropriate 3-substituted benzoic acids ($R^1$=F, Cl, MeO, Me, vinyl) gave desired products 4 in 71–81% yields. Removal of all TES groups of 4 followed by selective protection of the C-7 hydroxyl group of baccatin and subsequent selective acylation at the C-10 position afforded the corresponding 5 in 71–95% yields (Scheme 1). However, the esterification of baccatin 3 with 3-azidobenzoic acid, (Carnazzi, E., et al., *J. Med. Chem.* 1994, 37, 1841–1849; Georg, G. I. et al., *Bioorg Med. Chem. Lett.* 1995, 5, 615–620) gave the desired product 4 ($R^1$=$N_3$) as a minor product with D-ring opened compound(s) as the major product(s) that can be separated at a later stage. It is likely that the poor yield of this reaction is due to the steric hindrance of the 3-azido group. The baccatin 5 ($R^1$=$N_3$, $R^2$=Et) was obtained in 14% overall yield from 3. Propanoyl. acetyl, and cyclopropanecarbonyl groups were chosen as the 10-acyl substituents since these substituents showed excellent results in the structure-activity relationship study of the second generation taxoids.

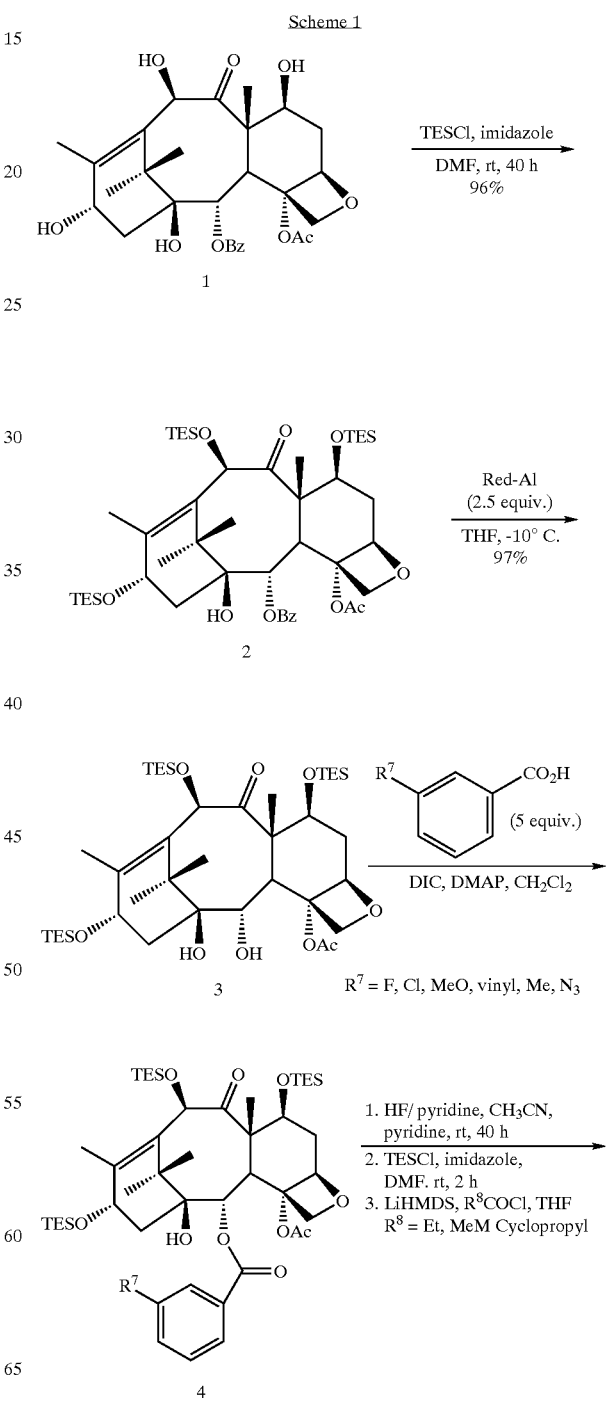

Scheme 1

EXAMPLES 35–51

As shown in Scheme 2 below, enantiopure β-lactams 6 with various C-4 substituents were readily obtained through efficient chiral ester enolate-imine cyclocondensations, followed by removal of the p-methoxyphenyl (PMP) group and subsequent protection as their tert-butyl carbamates (Ojima, I., et al., *Bioorg. Med. Chem. Lett.* 1993, 3, 2479–2482). The coupling reactions of baccatin 5 with β-lactam 6 following our standard protocol (Ojima, I., et al., *Tetrahedron Lett.* 1993, 34, 4149–4152) proceeded smoothly to give the corresponding new taxoids 7a–q (see Table 3 for structures) after deprotection of the silyl groups (Scheme 2).

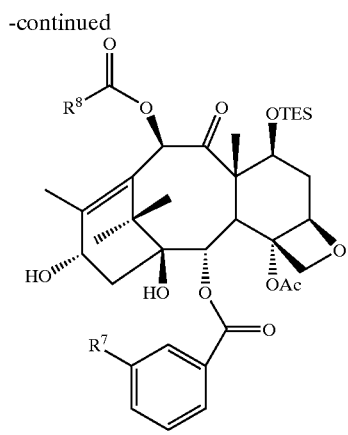

Scheme 2

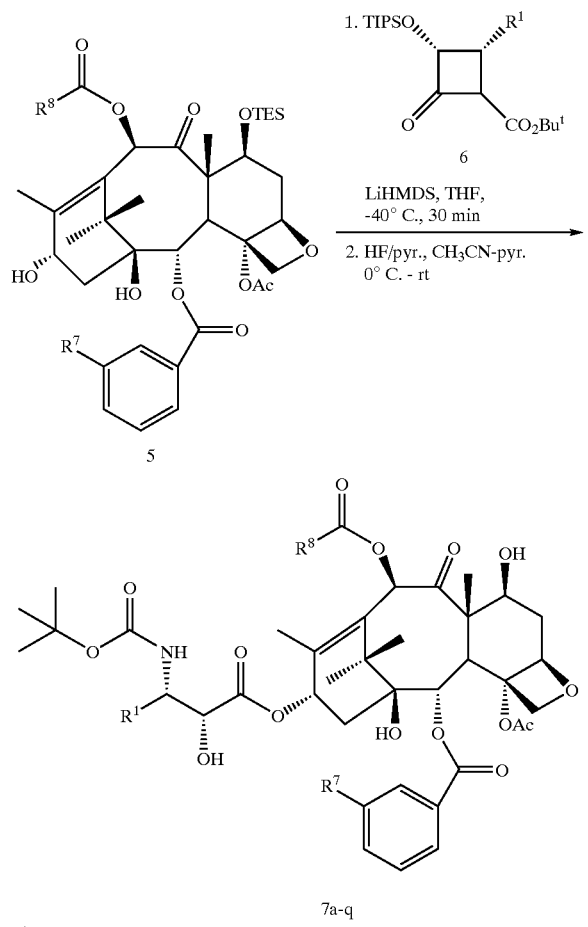

R¹ = isobutyl, isobutenyl, 1-propenyl, 3-butenyl, CF₂H, (S)-2,2-dimethylcyclopropyl

EXAMPLE 35

3'-Dephenyl-3'-(2-methylpropyl)-2-debenzoyl-2-(3-fuorobenzoyl)-10-propanoyldocetaxel (7a)

mp 138–140° C.; $[\alpha]^{20}_D$ –78.7 (c 0.47, CHCl₃); ¹H NMR (CDCl₃) δ 0.95 (s, 3 H), 0.97 (s, 3 H), 1.13 (s, 3 H), 1.28 (m, 18 H), 1.66 (m, 5 H), 2.37 (m, 6 H), 2.52 (m, 4 H), 3.21 (bs, 1 H), 3.80 (d, J=7.0 Hz, 1 H), 4.12 (m, 2 H), 4.29 (d, J=8.5 Hz, 1 H), 4.42 (m, 1 H), 4.57 (d, J=9.7 Hz, 1 H), 4.96 (d, J=10.1 Hz, 1 H), 5.61 (d, J=6.8 Hz, 1 H), 6.16 (t, J=8.4 Hz, 1 H), 6.30 (s, 1 H), 7.29 (m, 1 H), 7.43 (m, 1 H), 7.77 (d, J=9.1 Hz, 1 H), 7.89 (d, J=7.8 Hz, 1 H); ⁻C NMR (CDCl₃) δ 9.1, 9.5, 14.9, 21.8, 22.4, 23.2, 24.7, 26.5, 27.6, 28.1, 35.5, 41.2, 43.2, 45.6, 51.3, 57.6, 72.2, 72.6, 73.0, 75.4, 75.5, 76.2, 79.2, 79.6, 81.0, 84.4, 116.8, 117.2, 120.6, 120.9, 126.0, 130.3, 130.4, 142.6, 155.5, 169.9, 174.0, 174.6, 203.7. ¹⁹F NMR (CDCl₃, using Freon as standard) δ-112.1. HRMS (FAB) m/e calcd for $C_{44}H_{60}O_{15}FN.H^+$: 862.4025. Found: 862.4022 (Δ=+0.4 ppm).

EXAMPLE 36

3'-Dephenyl-3'-(2-methylprop-1-enyl)-2-debenzoyl-2-(3-fluorobenzoyl)-10-propanoyldocetaxel (7b)

mp 137–139° C.: $[\alpha]^{20}_D$ –77.8 (c 0.45, CHCl₃); ¹H NMR (CDCl₃) δ 1.13 (s, 3 H), 1.19 (m, 6 H), 1.33 (m, 9 H), 1.66 (s, 3 H), 1.75 (s, 6 H), 1.89 (s, 3 H), 2.34 (m, 5 H), 2.52 (m, 4 H), 3.37 (m, 1 H), 3.80 (d, J=7.0 Hz, 1 H), 4.12 (m, 2 H), 4.29 (d, J=8.5 Hz, 1 H), 4.42 (m, 1 H), 4.76 (m, 1 H), 4.96 (d, J=8.1 Hz, 1 H), 5.29 (m, 1 H), 5.63 (d, J=7.2 Hz, 1 H), 6.16 (t, J=8.4 Hz, 1 H), 6.30 (s, 1 H), 7.29 (m, 1 H), 7.43 (m, 1 H), 7.77 (d. J=9.1 Hz, 1 H), 7.89 (d, J=7.8 Hz, 1 H); ¹³C NMR (CDCl₃) δ 9.1, 9.5, 14.9, 18.5, 21.8, 22.3, 25.7, 26.6, 27.6, 28.2, 35.5, 43.1, 45.6, 51.6, 58.5, 72.2, 73.7, 75.4, 76.3, 77.6, 79.2, 79.9, 81.0, 84.4, 116.8, 117.1, 120.6, 125.9, 130.3, 130.4, 132.8, 138.0, 142.6, 155.4, 165.7, 170.0, 174.6, 203.7. ¹⁹F NMR (CDCl₃, using Freon as standard) δ-112.1. HRMS (FAB) m/e calcd for $C_{44}H_{58}O_{15}FN.H^+$: 860.3869. Found: 860.3870 (Δ=–0.1 ppm).

EXAMPLE 37

3'-Dephenyl-3'-(2-methylpropyl)-2-debenzoyl-2-(3-chlorobenzoyl)-10-propanoyldocetaxel (7c)

mp 143–145° C.; $[\alpha]^{20}_D$ –83.3 (c 0.12, CHCl₃); ¹H NMR (CDCl₃) δ 0.95 (m, 6 H), 1.12 (s, 3 H), 1.28 (m, 26 H), 1.66 (m, 6 H), 1.88 (s, 3 H), 2.37 (m, 6 H), 2.52 (m, 4 H), 3.21 (bs, 1 H), 3.80 (d, J=7.1 Hz, 1 H), 4.12 (m, 2 H), 4.27 (d, J=8.3 Hz, 1 H), 4.40 (dd, J=10.6, 6.8 Hz, 1 H), 4.57 (d, J=9.6 Hz, 1 H), 4.96 (d, J=8.1 Hz, 1 H), 5.60 (d, J=7.1 Hz, 1 H), 6.13 (t, J=8.8 Hz, 1 H), 6.30 (s, 1 H), 7.40 (t, J=7.8 Hz, 1 H), 7.56 (d, J=8.3 Hz, 1 H), 7.97 (d, J=7.7 Hz, 1 H), 8.10 (s, 1 H); ¹³C NMR (CDCl₃) δ 9.0, 9.5, 14.9, 21.8, 22.3, 23.2, 24.6, 26.5, 27.5, 28.1, 35.5, 41.2, 43.1, 45.6, 51.3, 58.4, 72.2, 72.6, 73.0, 75.4, 75.5, 76.2, 79.2, 79.6, 81.0, 84.4, 128.3, 130.0, 130.3, 131.0, 132.7, 133.6, 134.7, 142.6, 155.5, 165.5, 169.8, 174.0, 174.6, 203.7. HRMS: m/e calcd for $C_{44}H_{60}O_{15}NCl.H^+$: 878.3730. Found: 878.3728 (Δ=0.2 ppm).

EXAMPLE 38

3'-Dephenyl-3'-(2-methylprop-1-enyl)-2-debenzoyl-2-(3-chlorobenzoyl)-10-propanoyldocetaxel (7d)

mp 142–144° C.; $[\alpha]^{20}_D$ –88.9 (c 0.09, CHCl$_3$); $^1$H NMR (CDCl$_3$) δ 1.13 (s. 3 H), 1.21 (m, 7 H), 1.33 (s, 9 H), 1.66 (m, 3 H), 1.74 (m, 7 H), 1.82 (s, 3 H), 2.45 (m, 5 H), 2.52 (m, 3 H), 3.80 (d, J=7.1 Hz, 1 H), 4.12 (m, 2 H), 4.27 (d, J=8.3 Hz, 1 H), 4.40 (dd, J=10.6, 6.5 Hz, 1 H), 4.75 (m, 2 H), 4.96 (d, J=8.2 Hz, 1 H), 5.30 (d, J=9.2 Hz, 1 H), 5.60 (d, J=7.1 Hz, 1 H), 6.13 (t, J=8.6 Hz, 1 H), 6.30 (s, 1 H), 7.40 (t, J=7.8 Hz, 1 H), 7.56 (d, J=8.3 Hz, 1 H), 7.97 (d, J=7.7 Hz, 1 H), 8.10 (s, 1 H); $^{13}$C NMR (CDCl$_3$) δ 9.0, 9.5, 14.9, 18.6, 21.8, 22.3, 25.6, 26.5, 27.5, 28.1, 35.5, 41.2, 43.1, 45.6, 51.6, 58.4, 72.2, 72.3, 73.7, 75.4, 75.5, 76.3, 79.2, 79.9, 81.0, 84.4, 120.5, 128.3, 130.0, 130.2, 131.0, 132.7, 133.6, 134.7, 137.9, 142.6, 155.4, 165.5, 169.9, 173.1, 174.6, 203.7. HRMS: m/e calcd for $C_{44}H_{58}O_{15}NCl.H^+$: 876.3573. Found: 876.3573 (Δ=0.0 ppm).

EXAMPLE 39

3'-Dephenyl-3'-(2-methylpropyl)-2-debenzoyl-2-(3-methoxybenzoyl)-10-propanoyldocetaxel (7e)

mp 132–134° C.; $[\alpha]^{20}_D$ –114.3 (c 0.07, CHCl$_3$); $^1$H NMR (CDCl$_3$) δ 0.95 (m, 6 H), 1.13 (s, 3 H), 1.28 (m, 8 H), 1.66 (m, 6 H), 1.88 (s, 3 H), 2.37 (m, 6 H), 2.52 (m, 4 H), 3.21 (bs, 1 H), 3.80 (d, J=6.9 Hz, 1 H), 3.86 (s, 3 H), 4.12 (m, 2 H), 4.30 (d, J=8.4 Hz, 1 H), 4.40 (dd, J 10.6, 6.8 Hz, 1 H), 4.57 (d, J=9.6 Hz, 1 H), 4.96 (d, J=8.1 Hz, 1 H), 5.63 (d, J=7.0 Hz, 1 H), 6.16 (t, J=8.4 Hz, 1 H), 6.30 (s, 1 H), 7.13 (d, J=7.9 Hz, 1 H), 7.33 (t, J=8.0 Hz, 1 H), 7.62 (s, 1 H), 7.68 (d, J=7.6 Hz, 1 H); $^{13}$C NMR (CDCl$_3$) δ 9.0, 9.6, 14.9, 21.8, 22.5, 23.3, 24.7, 26.6, 27.6, 28.1, 35.5, 41.2, 43.2, 45.6, 51.2, 55.3, 58.5, 72.2, 72.6, 73.0, 75.4, 75.5, 76.2, 79.1, 79.7, 81.1, 84.4, 114.1, 120.4, 122.7, 129.6, 130.4, 132.9, 142.5, 155.4, 159.6, 166.8, 169.9, 174.0, 174.6, 203.8. HRMS: m/e calcd for $C_{45}H_{63}O_{16}N.H^+$: 874.4225. Found: 874.4224 (Δ=0.1 ppm).

EXAMPLE 40

3'-Dephenyl-3'-(2-methylprop-1-enyl)-2-debenzoyl-2-(3-methoxybenzoyl)-10-propanoyldocetaxel (7f)

mp 130–132° C.; $[\alpha]^{20}_D$ –75.0 (c 0.08, CHCl$_3$); $^1$H NMR (CDCl$_3$) δ 1.13 (s, 3 H), 1.28 (m, 8 H), 1.33 (s, 9 H), 1.66 (m, 3 H), 1.73 (s, 3 H), 1.75 (s, 3H), 1.89 (m, 5 H), 2.37 (m, 6 H), 2.52 (m, 3 H), 3.80 (d, J=6.9 Hz, 1 H), 3.86 (s, 3 H), 4.12 (m, 2 H), 4.32 (d, J=8.5 Hz, 1 H), 4.40 (dd, J=10.6, 6.8 Hz, 1 H), 4.72 (m, 2 H), 4.96 (d, J=8.3 Hz, 1 H), 5.30 (d, J=7.6 Hz, 1 H), 5.64 (d, J=7.0 Hz, 1 H), 6.16 (t, J=8.6 Hz, 1 H), 6.30 (s, 1 H), 7.13 (d, J=7.9 Hz, 1 H), 7.33 (t, J=8.0 Hz, 1 H), 7.62 (s, 1 H), 7.68 (d, J=7.6 Hz, 1 H); $^{13}$C NMR CDCl$_3$) δ 9.0, 9.5, 14.9, 18.5, 21.8, 22.4, 25.7, 26.6, 27.5, 28.2, 35.5, 43.2, 45.6, 51.5, 55.3, 58.5, 72.2, 72.3, 73.7, 75.1, 75.4, 76.2, 79.1, 79.9, 81.1, 84.4, 114.6, 120.1, 120.6, 122.5, 129.6, 130.4, 132.9, 137.8, 142.5, 155.4, 159.6, 166.8, 170.0, 174.0, 174.6, 203.8. HRMS: m/e calcd for $C_{45}H_{61}O_{16}N\ H^-$: 872.4069. Found: 872.4072 (Δ=–0.4 ppm).

EXAMPLE 41

3'-Dephenyl-3'-difluoromethyl-2-debenzoyl-2-(3-methoxybenzoyl)-10-propanoyldocetaxel (7g)

mp 132–134° C.; $[\alpha]^{20}_D$ –70.0 (c 0.47, CHCl$_3$); $^1$H NMR (CDCl$_3$) δ 0.95 (m, 6H), 1.12 (s, 3 H), 1.28 (m, 26 H), 1.66 (m, 6 H), 1.88 (s, 3 H), 2.37 (m, 5 H), 2.52 (m, 4 H), 3.18 (bs, 1 H), 3;82 (d, J=6.9 Hz, 1 H), 4.12 (m, 4 H), 4.31 (d, J=8.4 Hz, 1 H), 4.40 (dd, J=10.2, 6.6 Hz, 1 H), 4.56 (d, J=9.6 Hz, 1 H), 4.97 (d, J=8.7 Hz, 1 H), 5.65 (d, J=6.9 Hz, 1 H), 6.14 (t, J=8.4 Hz, 1 H), 6.31 (s, 1 H), 7.23 (m, 1 H), 7.46 (t, J=7.8 Hz, 1 H), 7.88 (d, J=7.5 Hz, 1 H); $^{13}$C NMR (CDCl$_3$) δ 9.0, 9.5, 14.9, 21.8, 22.5, 23.2, 24.7, 26.6, 27.6, 28.1, 35.5, 41.2, 43.2, 45.6, 51.4, 58.5, 72.2, 72.6, 73.0, 75.4, 75.5, 76.3, 78.0, 79.2, 79.7, 81.0, 84.4, 120.2, 124.3, 126.8, 130.1, 132.8, 140.8, 142.6, 155.5, 166.0, 170.1, 14.0, 174.6, 203.8. HRMS: m/e calcd for $C_{44}H_{60}O_{15}N_4.H^+$: 885.4133. Found: 885.4134 (Δ=–0.1 ppm).

EXAMPLE 42

3'-Dephenyl-3'-(3-butenyl)-2-debenzoyl-2-(3-methoxybenzoyl)-10-propanoyldocetaxel (7h)

mp 128–130° C.; $[\alpha]^{20}_D$ –70.5 (c 0.44, CHCl$_3$); $^1$H NMR (CDCl$_3$) δ 1.14 (s, 3 H), 1.25 (m, 9 H), 1.34 (s, 9 H), 1.66–1.73 (m, 12 H), 1.89 (s, 3 H), 2.37 (m, 5H), 2.52 (m, 4 H), 3.32 (bs, 1 H), 3.81 (d, J=6.9 Hz, 1 H), 4.12 (m, 2 H), 4.30 (d, J=8.1 Hz, 1 H), 4.40 (dd, J=10.6, 6.8 Hz, 1 H), 4.74 (m, 2 H), 4.96 (d, J=8.2 Hz, 1 H), 5.29 (m, 1 H), 5.64 (d, J=7.0 Hz, 1 H), 6.13 (t, J=9.0 Hz, 1 H), 6.31 (s, 1 H), 7.23 (d, J=7.5 Hz, 1 H), 7.46 (t, J=7.9 Hz, 1 H), 7.78 (s, 1 H), 7.86 (d, J=7.8 Hz, 1 H); $^{13}$C NMR (CDCl$_3$) δ 9.0, 9.5, 15.0, 18.6, 21.8, 22.5, 25.7, 26.6, 27.6, 28.2, 35.5, 43.2, 45.6, 51.6, 58.6, 72.2, 72.6, 73.7, 75.4, 76.4, 79.2, 81.0, 84.5, 87.3, 120.1, 120.5, 124.3, 126.8, 130.2, 132.7, 140.8, 166.0, 170.1, 174.6, 203.8. HRMS: m/e calcd for $C_{44}H_{58}O_{15}N4.H^+$: 883.3977. Found: 883.3987 (Δ=–1.1 ppm).

EXAMPLE 43

3'-Dephenyl-3'-(2-propenyl)-2-debenzoyl-2-(3-methoxybenzoyl)-10-propanoyldocetaxel (7i)

mp 127–130° C.; $[\alpha]^{20}_D$ –64.0 (c 0.25, CHCl$_3$); $^1$H NMR (CDCl$_3$) δ 0.87 (m, 3 H), 1.13 (s, 3 H), 1.21 (m, 26 H), 1.66 (m, 3 H), 1.88 (s, 3 H), 2.20–2.37 (m, 5 H), 2.52 (m, 3 H), 3.39 (bs, 1 H), 3.80 (d, J=8.8 Hz, 1 H), 3.89 (s, 3 H), 4.12 (m, 2 H), 4.35 (m, 3 H), 4.61 (m, 1 H), 4.96 (m, 2 H), 5.63 (m, 1.25 H), 5.84 (d, J=5.8 Hz, 0.5 H), 6.06 (d, J=5.9 Hz, 0.25 H), 6.23 (t, J=8.8 Hz, 1 H), 6.30 (s, 1 H), 7.13 (d, J=5.8 Hz, 1 H), 7.38 (t, J=8.0 Hz, 1 H), 7.63 (s, 1 H), 7.70 (d, J=7.6 Hz, 1 H); $^{13}$C NMR (CDCl$_3$) δ 9.0, 9.6, 14.8, 21.9, 22.5, 26.7, 27.6, 28.0, 29.7, 35.5, 43.2, 45.7, 55.3, 58.6, 68.5, 72.2, 73.0, 75.1, 75.3, 79.0, 81.2, 84.5, 87.4, 103.1, 114.1, 120.7, 122.7, 129.8, 130.2, 133.3, 159.7, 167.1, 170.3, 170.7, 174.6, 203.6. Anal. Calcd for $C_{42}H_{55}O_{16}N_1F_2$: C, 58.12; H, 6.39; N, 1.61. Found: C, 58.07; H, 6.57; N, 1.55.

EXAMPLE 44

3'-Dephenyl-3'-[(S)-2,2-dimethylcyclopropyl]-2-debenzoyl-2-(3-methoxybenzoyl)-10-propanoyldocetaxel (7j)

mp 115–118° C.; $[\alpha]^{20}_D$ –53.9 (c 0.65, CHCl$_3$); $^1$H NMR (CDCl$_3$) δ 1.14 (s, 3 H), 1.23 (t, J=7.5 Hz, 3 H), 1.25 (s, 3 H), 1.30 (s, 9 H), 1.39 (m, 2 H), 1.67 (s, 3 H), 1.84 (m, 1 H), 1.88 (s, 3 H), 2.15 (m, 2 H), 2.33 (m, 2 H), 2.37 (s, 3 H), 2.53 (m, 3 H), 3.26 (bs, 1 H), 3.81 (s, J=6.9 Hz, 1 H), 3.89 (s, 3 H), 4.05 (m, 1 H), 4.18 (d, J=8.1 Hz, 1 H), 4.23 (s, 1 H), 4.36 (d, J=8.4 Hz, 1 H), 4.44 (dd, J=7.2, 10.2 Hz, 1 H), 5.66 (d, J=7.2 Hz, 1H), 5.82 (m, 1H), 6.21 (t, J=8.7 Hz, 1H), 6.31 (s, 1H), 7.14 (dd, J=2.4, 8.1 Hz, 1 H), 7.39 (t, J=8.1 Hz, 1 H), 7.65 (s, 1 H), 7.72 (d, J=7.5 Hz, 1 H); $^{13}$C NMR (CDCl$_3$)

δ 9.0, 9.5, 14.9, 21.9, 22.6, 26.7, 27.6, 28.1, 29.7, 30.1, 31.4, 35.5, 35.6, 43.2, 45.6, 52.4, 55.4, 58.6, 72.2, 72.5, 75.4, 79.1, 79.8, 81.1, 84.4, 114.4, 115.8, 120.3, 122.7, 129.7, 130.4, 132.9, 137.2, 142.4, 155.4, 159.6, 166.9, 170.0, 173.9, 174.6, 203.8. HRMS (FAB) m/z calcd for $C_{45}H_{61}NO_{16}Na^+$: 894.3870. Found: 894.3904 (Δ=−3.6 ppm).

EXAMPLE 45

3'-Dephenyl-3'-[(E)-prop-1-enyl]-2-debenzoyl-2-(3-methoxybenzoyl)-10-propanoyldocetaxel (7k)

mp 142–144° C.; $[\alpha]^{20}_D$−71.8 (c 0.7, CHCl$_3$); $^1$H NMR (CDCl$_3$) δ 1.15 (s, 3 H), 1.26 (s, 3 H), 1.34 (s, 9 H), 1.68 (s, 3 H), 1.74 (s, 3 H), 1.77 (s, 3 H), 1.90 (s, 3 H), 1.92 (m, 1 H), 2.24 (s, 3 H), 2.35 (s, 3 H), 2.38 (m, 2 H), 2.54 (m, 1 H), 3.81 (d, J=6.9 Hz, 1 H), 3.87 (s, 3 H), 4.18 (d, J=8.4 Hz, 1 H), 4.35 (d, J=8.4 Hz, 1 H), 4.43 (dd, J=6.6, 10.5 Hz, 1 H), 4.75 (bs, 2 H), 4.97 (d, J=8.1 Hz, 1 H), 5.32 (s, 1 H), 5.66 (d, J=7.2 Hz, 1 H), 6.18 (t, J=8.4 Hz, 1 H), 6.30 (s, 1 H), 7.14 (dd, J=2.1, 8.1 Hz, 1 H), 7.38 (t, J=7.8 Hz, 1 H), 7.64 (s, 1 H), 7.70 (d, J=7.8 Hz, 1 H); $^{13}$C NMR (CDCl$_3$) δ 9.5, 15.0, 18.5, 20.9, 21.8, 22.4, 25.7, 26.7, 28.2, 29.7, 35.6, 43.2, 45.6, 51.5, 55.4, 58.6, 72.2, 72.3, 73.7, 75.1, 75.6, 76.4, 79.1, 80.0, 81.1, 84.4, 114.6, 120.2, 122.6, 122.6, 129.6, 130.4, 132.8, 137.9, 142.7, 143.5, 159.7, 166.8, 170.0, 171.3, 173.1, 203.8. HRMS (FAB) m/z calcd for $C_{44}H_{59}NO_{16}.Na^+$: 880.3732. Found: 880.3766 (Δ=−3.9 ppm).

EXAMPLE 46

3'-Dephenyl-3'-(2-methylprop-1-enyl)-2-debenzoyl-2-(3-methoxybenzoyl)-10-acetyldocetaxel (7l)

mp 144–146° C.; $[\alpha]^{20}_D$−73.9 (c 0.92, CHCl$_3$); $^1$H NMR (CDCl$_3$) δ 1.16 (s, 3 H), 1.26 (s, 3 H), 1.34 (s, 9 H), 1.66 (m, 4 H), 1.67 (s, 3 H), 1.74 (s, 3 H), 1.77 (s, 3 H), 1.82 (m, 2 H), 1.89 (s, 3 H), 2.34 (s, 3 H), 2.38 (m, 2 H), 2.54 (m, 1 H), 3.36 (bs, 1 H), 3.81 (d, J=7.2 Hz, 1 H), 3.87 (s, 3 H), 4.18 (d, J=9.0 Hz, 1 H), 4.20 (s, 1 H), 4.34 (d, J=8.4 Hz, 1 H), 4.41 (dd, J=6.6, 11.1 Hz, 1H), 4.79 (m, 2H), 4.97 (d, J=9.0 Hz, 1 H), 5.31 (bs, 1 H), 5.66 (d, J=6.9 Hz, 1 H), 6.18 (t, J=9.0 Hz, 1 H), 6.30 (s, 1 H), 7.14 (d, J=8.1 Hz, 1 H), 7.37 (t, J=7.8 Hz, 1 H), 7.64 (s, 1 H), 7.70 (d, J=7.5 Hz, 1 H); $^{13}$C NMR (CDCl$_3$) δ 9.5, 13.0, 15.0, 18.5, 21.9, 22.4, 25.7, 26.7, 28.2, 29.7, 35.5, 35.6, 43.2, 45.6, 51.5, 55.4, 58.6, 72.2, 72.4, 73.7, 75.1, 75.6, 76.4, 79.2, 80.0, 81.1, 84.4, 114.6, 120.1, 120.6, 122.6, 129.6, 130.4, 132.9, 137.9, 142.7, 155.4, 159.7, 166.8, 170.0, 171.9, 175.1, 203.9. HRMS (FAB) m/z calcd for $C_{46}H_{61}NO_{16}.Na^+$: 906.3888. Found: 906.3909 (Δ=−2.3 ppm).

EXAMPLE 47

3'-Dephenyl-3'-(2-methylprop-1-enyl)-2-debenzoyl-2-(3-methoxybenzoyl)-10-cyclopropyldocetaxel (7m)

mp 118–120° C.; $[\alpha]^{20}_D$−52.3 (c 1.0, CHCl$_3$); $^1$H NMR (CDCl$_3$) δ 1.15 (s, 3 H), 1.21 (t, J=7.4 Hz, 3 H), 1.23 (s, 3 H), 1.34 (s, 9 H), 1.68 (s, 3 H), 1.75 (s, 3 H), 1.77 (s, 3 H), 1.86 (m, 1 H), 1.90 (s, 3 H), 2.36 (s, 6 H), 2.39 (m, 2 H), 2.53 (m, 3 H), 3.36 (bs, 1 H), 3.83 (d, J=6.9 Hz, 1 H), 4.19 (m, 3 H), 4.32 (d, J=8.4 Hz, 1H), 4.43 (dd, J=6.6, 10.5 Hz, 1H), 4.74 (d, J=3.0 Hz, 1H), 4.97 (d, J=8.4 Hz, 1 H), 5.34 (d, J=10.8 Hz, 2 H), 5.67 (d, J=6.9 Hz, 1 H), 5.8 (d, J=17.4 Hz, 1 H), 6.18 (t, J=8.4 Hz, 1 H), 6.32 (s, 1 H), 6.76 (dd, J=10.5, 17.4 Hz, 1 H), 7.44 (t, J=7.8 Hz, 1 H), 7.63 (d, J=7.5 Hz, 1 H), 7.98 (d, J=7.8 Hz, 1 H), 8.17 (s, 1 H); $^{13}$C NMR (CDCl$_3$) δ 9.0, 9.5, 15.0, 18.5, 20.9, 21.8, 22.4, 25.7, 26.7, 28.2, 29.7, 35.6, 43.2, 45.6, 51.5, 58.6, 72.2, 72.9, 73.7, 75.1, 75.4, 76.4, 79.2, 80.0, 81.1, 84.4, 115.4, 120.6, 127.8, 128.9, 129.4, 129.5, 131.3, 135.9, 138.1, 155.4, 159.7, 165.4, 166.9, 170.0, 171.9, 178.5, 203.8. HRMS (FAB) m/z calcd for $C_{46}H_{61}NO_{15}.Na^+$: 890.3939. Found: 890.3981 (Δ=−4.7 ppm).

EXAMPLE 48

3'-Dephenyl-3'-(2-methylpropyl)-2-debenzoyl-2-(3-azidobenzoyl)-10-propanoyldocetaxel (7n)

mp: 136–138° C.; $[\alpha]^{20}_D$−110.6 (c 0.05, CHCl$_3$); $^1$H NMR (CDCl$_3$) δ 1.14 (s, 3 H), 1.23 (m, 8 H), 1.30 (s, 3 H), 1.67 (s, 3 H), 1.88 (s, 3 H), 2.35 (m, 9 H), 2.53 (m, 2 H), 3.80 (d, J=6.9 Hz, 1 H), 3.89 (s, 3 H), 4.08 (m, 1 H), 4.16 (d, J=8.4 Hz, 1 H), 4.30 (bs, 1 H), 4.36 (d, J=8.7 Hz, 1 H), 4.40 (m, 1 H), 4.69 (d, J=9.3 Hz, 1 H), 4.97 (d, J=8.4 Hz, 1 H), 5.19 (m, 2 H), 5.66 (d, J=7.2 Hz, 1 H), 5.78 (m, 1 H), 6.19 (t, J=8.7 Hz, 1 H), 6.31, (s, 1 H), 7.14 (m, 1 H), 7.40 (t, J=8.1 Hz, 1 H), 7.68 (m, 2 H); $^{13}$C NMR (CDCl$_3$) δ 9.0, 9.5, 14.9, 21.9, 22.7, 26.6, 27.5, 28.1, 35.4, 35.6, 36.4, 43.2, 45.6, 52.8, 55.4, 58.6, 71.2, 72.2, 72.6, 75.1, 75.4, 76.5, 79.1, 81.2, 84.4, 114.3, 118.9, 120.5, 122.7, 129.7, 130.3, 132.9, 133.6, 142.5, 159.7, 167.0, 170.0, 174.6, 203.9. HRMS (FAB) m/z calcd for $C_{44}H_{59}NO_{16}.Na^+$: 880.3732. Found: 880.3761 (Δ=−2.9 ppm).

EXAMPLE 49

3'-Dephenyl-3'-(2-methylprop-1-enyl)-2-debenzoyl-2-(3-azidobenzoyl)-10-propanoyldocetaxel (7o)

mp: 128–130° C.; $^1$H NMR (CDCl$_3$) d 0.098 (t, J=4.6 Hz, 1 H), 0.62 (dd, J=8.5. 4.3 H), 1.11 (m, 10 H), 1.24 (s, 6 H), 1.31 (s, 9 H), 1.66 (s, 3 H), 1.83 (s, 1 H), 1.89 (s, 3 H), 2.34 (s, 3 H), 2.37 (m, 2 H), 2.54 (m, 3 H), 3.34 (d, J=6.6 Hz, 1 H), 3.51 (t, J=9.3 Hz, 1 H), 3.80 (d, J=7.0 Hz, 1 H), 3.85 (s, 3 H), 4.18 (d, J=8.4 Hz, 1 H), 4.32 (s, 1 H), 4.34 (d, J=8.4 Hz, 1 H), 4.43 (m, 1 H), 4.80 (d, J=8.9 Hz, 1 H), 4.97 (d, J=8.4 Hz, 1 H), 5.65 (d, J=7.0 Hz, 1 H), 6.15 (t, J=8.6 Hz, 1 H), 6.30 (s, 1 H), 7.13 (dd, J=8.0, 2.2 Hz, 1 H), 7.36 (t, J=8.0 Hz, 1 H), 7.63 (s, 1 H), 7.69 (d, J=7.5 Hz, 1 H); $^{13}$C NMR (CDCl$_3$) d 9.0, 9.5, 14.9, 17.1, 19.3, 20.1, 22.0, 22.6, 26.2, 26.5, 27.1, 27.5, 28.1, 33.2, 35.5, 43.2, 45.5, 55.3, 55.4, 58.5, 72.1, 72.7, 73.0, 75.1, 75.4, 76.4, 79.1, 79.8, 81.1, 84.4, 87.4, 114.4, 120.3, 122.6, 129.6, 130.4, 132.8, 142.6, 155.0, 159.6, 166.7, 169.7, 170.6, 174.6, 203.8. HRMS (FAB) m/z calcd for $C_{46}H_{63}NO_{16}.H^+$: 886.4225. Found: 886.4237 (Δ=−1.3 ppm).

EXAMPLE 50

3'-Dephenyl-3'-(2-methylprop-1-enyl)-2-debenzoyl-2-(3-ethenylbenzoyl)-10-propanoyldocetaxel (7p)

mp: 120–122° C.; $[\alpha]^{20}_D$−100.0; $^1$H NMR (CDCl$_3$) δ 1.14 (s, 3 H), 1.32 (s, 3 H), 1.66 (s, 3 H), 1.73 (s 3 H), 1.75 (s, 3 H), 1.88 (s, 3 H), 2.36 (m, 6 H), 3.87 (s, 2 H), 4.12 (d, 2 H), 4.27 (m, 2 H), 4.40 (dd, J=10.6, 6.8 Hz, 1 H) 4.57 (bs, 1 H), 4.86 (d, 1 H), 4.96 (d, J=8.1 Hz, 1 H), 5.60 (m, 2 H), 6.13 (t, J=8.8 Hz, 1 H), 6.30 (s, 1 H), 7.40 (t, J=7.8 Hz, 1 H), 7.56 (d, J=8.3 Hz, 1 H), 7.97 (d, J=7.7 Hz, 1 H), 8.10 (s, 1 H); $^{13}$C NMR (CDCl$_3$) δ 4.5, 5.0, 10.4, 13.3, 17.3, 18.0, 22.2, 23.0, 23.6, 25.2, 30.9, 31.1, 38.7, 41.1, 50.9, 54.1, 67.7, 68.6, 70.5, 70.9, 73.2, 74.5, 76.6, 79.9, 110.0, 115.8, 118.1, 122.8, 124.3, 125.2, 128.0, 138.0, 149.0, 162.0, 165.5, 170.0, 199.0. HRMS: m/e calcd for $C_{39}H_{56}O_{12}Si.H^+$: 828.380646. Found: 828.380700 (Δ=−0.1 ppm).

EXAMPLE 51

3'-Dephenyl-3'-(2-methylprop-1-enyl)-2-debenzoyl-2-(3-methylbenzoyl)-10-acetyldocetaxel (7q)

mp 145–148° C.; $[\alpha]^{20}{}_D$ –85.4 (c 0.011, CHCl$_3$); $^1$H NMR (CDCl$_3$) δ 1.14 (s, 3 H), 1.25 (s, 3 H), 1.340 (s, 9 H), 1.67 (s, 3 H), 1.75 (d, J=3.6 Hz, 6 H), 1.89 (s, 3 H), 2.23 (s, 3 H), 2.37 (m, 9 H), 2.52 (m, 2 H), 3.80 (d, J=7.2 Hz, 1 H), 4.18 (m, 2 H), 4.30 (d, J=8.7 Hz, 1 H), 4.42 (m, 1 H), 4.75 (m, 2 H), 4.96 (d, J=7.8 Hz, 1 H), 5.29 (m, 2 H), 5.64 (d, J=7.2 Hz, 1 H), 6.16 (t, J=8.7 Hz, 1 H), 6.30 (s, 1 H), 7.37 (m, 2 H), 7.90 (m, 2 H); $^{13}$C (CDCl$_3$) δ 9.5, 14.9, 18.5, 20.8, 21.3, 21.8, 223,25.7, 26.6, 28.2, 35.6, 43.2, 25.6, 58.4, 72.1, 72.3, 73.7, 74.9, 75.6, 76.46, 79.1, 81.1, 84.4, 120.7, 127.3, 128.5, 129.1, 130.8, 132.8, 134.4, 138.3, 142.6, 155.4, 167.0, 170.0, 171.3, 203.7. HRMS (FAB) m/z calcd for $C_{44}H_{59}NO_{15} \cdot Na^+$: 864.3782. Found: 864.3803 (Δ=−2.4 ppm).

EXAMPLE 52

A cytotoxicity assay of these new second generation taxoids was performed on human breast cancer cell lines, LCC6-WT and LCC-MDR, and selected taxoids were also assayed for their potency against MCF7 and MCF7-R (Skehan, P., et al., *J. Nat. Cancer Inst.* 1990, 82, 1107–1112).

As Table 3 shows, these new taxoids exhibit two to three times higher potency against drug-sensitive cancer cell lines (LCC6-WT, MCF7) as compared to that of paclitaxel. Moreover, these taxoids exhibit 2–3 orders of magnitude higher potency against drug-resistant cancer cell lines (LCC6-MDR, MCF7-R) as compared to paclitaxel and docetaxel. The most characteristic feature of these new second generation taxoids is the very small difference in the IC$_{50}$ values between drug-sensitive and drug-resistant cell lines (R/S=0.89–7.0 except for 7g and 7i against MCF7 and MCF7-R). In some cases (7e and 7f), the taxoids show even slightly better activity against the drug-resistant cell lines than that against the drug-sensitive cell line, although this could be within experimental error.

This makes a sharp contrast with paclitaxel and docetaxel which show 2 orders of magnitude difference (R/S= 112–235) between the drug-sensitive and drug-resistant cell lines.

As for the structure-activity relationships of these taxoids on the 3(meta)-position of the C-2 benzoate, the cytotoxicity decreases in the order: F>Cl>MeO>N$_3$>Me>CH=CH$^2$ against drug-sensitive cell line LCC6-WT, while the order is MeO>N$_3$, F, Cl>Me>CH=CH$_2$ against drug-resistant cell line LCC6-MDR. A similar trend is observed against MCF7 and MCF7-R. Although it is known that 3-azidobenzoyl analogs possesses very high potency in the structure-activity relationship of paclitaxel, 3-methoxybenzoyl taxoids in these new second-generation-activity relationship of paclitaxel, 3-azidobenzoyl taxoids, especially against MCF7-R (compare 7e, 7f vs 7n, 7o). As observed earlier for the first series of the second generation taxoids, introduction of an n-propanoyl group at the C-10 position is effective against drug-resistant cell lines (7f vs 7l, 7m).

It has been previously observed that 3'-(2-prop-1-enyl) taxoids generally show better activity than 3'-(2-propyl) taxoids, (Ojima, I., et al., *J. Med. Chem.* 1996, 39, 3889–3896). In contrast to this observation, the new series of 3'-(2-propyl) taxoids (7a, 7c, 7e and 7n) and 3'-(2-prop-1-enyl) taxoids (7b, 7d, 7f, and 7o) of the present invention demonstrate essentially the same potency.

TABLE 3

Cytotoxicity of taxoids 7a–q (IC$_{50}$ nM)$^a$

| Taxoid | R$^7$ | R$^8$ | R$^1$ | LCC6-WT$^b$ | LCC6-MDR$^c$ | R/S$^d$ | MCF7$^e$ | MCF7-R$^f$ | R/S$^a$ |
|---|---|---|---|---|---|---|---|---|---|
| Paclitaxel | — | — | — | 3.1 | 346 | 112 | 1.7 | 300 | 177 |
| Docetaxel | — | — | — | 1.0 | 120 | 120 | 1.0 | 235 | 235 |
| 7a | F | Et | CH$_2$CH(CH$_3$)$_2$ | 0.4 | 2.4 | 6.0 | | | |
| 7b | F | Et | CH=C(CH$_3$)$_2$ | 0.5 | 2.1 | 4.2 | | | |
| 7c | Cl | Et | CH$_2$CH(CH$_3$)$_2$ | 0.8 | 2.9 | 3.6 | | | |
| 7d | Cl | Et | CH=C(CH$_3$)$_2$ | 0.8 | 1.3 | 1.6 | | | |
| 7e | MeO | Et | CH$_2$CH(CH$_3$)$_2$ | 0.9 | 0.8 | 0.89 | 0.36 | 0.43 | 1.19 |
| 7f | MeO | Et | CH=C(CH$_3$)$_2$ | 1.0 | 0.9 | 0.90 | 0.36 | 0.33 | 0.92 |
| 7g | MeO | Et | CF$_2$H | 1.5 | 4.7 | 3.1 | 0.4 | 4.3 | 10.8 |
| 7h | MeO | Et | CH$_2$CH$_2$CH=CH$_2$ | 0.9 | 5.4 | 6.0 | 2.0 | 7.7 | 3.9 |
| 7i | MeO | Et | CH$_2$CH=CH$_2$ | 1.2 | 8.4 | 7.0 | 0.8 | 8.7 | 10.9 |
| 7j | MeO | Et | (S)-2,2-dimethyl-cyclopropyl | 0.48 | 1.1 | 2.3 | 0.6 | 1.5 | 2.5 |
| 7k | MeO | Et | (E)-CH=CHCH$_3$ | 1.2 | 4.1 | 3.4 | | | |
| 7l | MeO | Me | CH=C(CH$_3$)$_2$ | 0.6 | 2.7 | 4.5 | 0.8 | 2.3 | 2.9 |
| 7m | MeO | c-Pr$^g$ | CH=C(CH$_3$)$_2$ | 1.0 | 2.9 | 2.9 | | | |
| 7n | N$_3$ | Et | CH$_2$CH(CH$_3$)$_2$ | 1.1 | 2.4 | 2.2 | 1.0 | 2.1 | 2.1 |
| 7o | N$_3$ | Et | CH=C(CH$_3$)$_2$ | 0.9 | 1.2 | 1.3 | 0.9 | 1.1 | 1.2 |
| 7p | CH=CH$_2$ | Et | CH=C(CH$_3$)$_2$ | 2.9 | 7.1 | 2.4 | | | |
| 7q | Me | Me | CH=C(CH$_3$)$_2$ | 1.5 | 5.8 | 3.9 | 0.8 | 5.0 | 6.3 |

$^a$The concentration of compound which inhibits 50% (IC$_{50}$, nM) of the growth of human tumor cell line after 72 h drug exposure.
$^b$LCC6-WT: human breast carcinoma.
$^c$LCC6-MDR: MDR1 transduced line.
$^d$Ratio of activities. drug-resistant (R) vs. drug-sensitive (S) cell lines.
$^e$MCF7: human breast carcinoma.
$^f$MCF7-R: multi-drug resistant human breast carcinoma
$^g$Cyclo-propyl.

These results confirm that the cytotoxicity of taxoids is highly sensitive to the structure of substituents at the C-3', C-10 and the C-2 benzoate positions. It is noteworthy that three of the newly developed second-generation taxoids, 7e, 7f, and 7o, show virtually no difference in activity against drug-resistant and drug-sensitive cell lines. These taxoids can be categorized as "advanced second generation taxoids," which are highly promising candidates for cancer chemotherapy.

EXAMPLE 53

Pharmaceutical preparations were prepared using the compounds, and their derivatives, shown by the following chemical formula (I) (SB-T-1213, 3'-dephenyl-3'-(2-methyl-1-propenyl)-10-propanoyldocetaxel), and formula (II) (3'-dephenyl-3'-(2,2-dimethyl-1-cyclopropyl)-10-acetyldocetaxel) respectively:

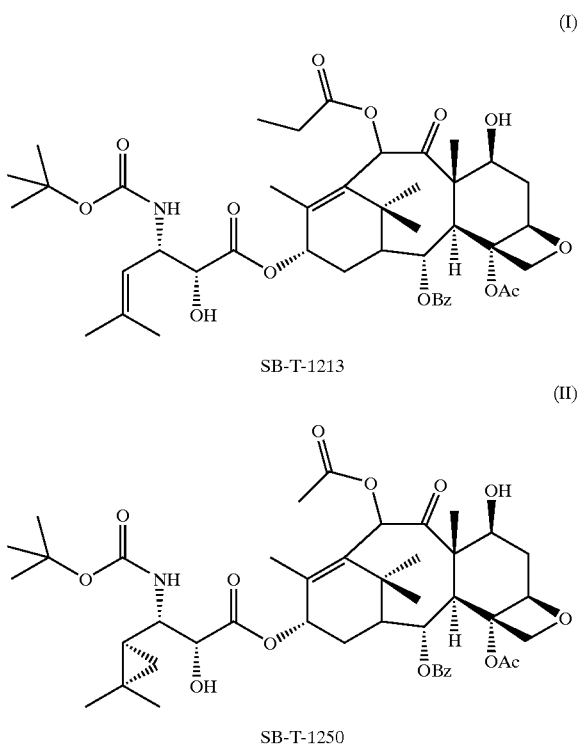

Derivatives of formula (I) include SB-T-121303 and SB-T-121304.

Inhibitory Concentration of Taxoids In Vitro

Growth inhibition effects of taxoids, SB-T-1213 and SB-T-1250, on cancer cells were assessed against a panel of seven human cancer cell lines, MCF-7wt, PC-3, DU145, NCIH23, WiDr, MCF-7 ADRr line, A2780, and expressed as their 50% inhibitory concentration, $IC_{50}$.

Cells were plated in 6-well flat bottom plates (Falcon, Lincoln Park, N.J.) at a concentration of $10^5$ cells $ml^{-1}$ in complete medium. After 24 h, the medium was replaced with media containing the test substances. Control cells were treated with vehicle alone. Cells were then washed twice and cultures maintained up to 72 h in complete medium (without removing the test substances). At this time point quadruplicate counts of triplicate cultures were performed. To calculate the growth inhibition effect, three independent experiments were performed for each test substance/cell line. The $IC_{50}$ values were then calculated by fitting the concentration-effect curve data obtained in the three experiments with the sigmoid-Emax model using nonlinear regression, weighted by the reciprocal of the square of the predicted effect according to the method of Motulsky, H. J. and Ransnas, L. A., *FASEB J.* 1:365–74 (1987).

The results from this study are summarized in Table 4. When considering results of the taxoids currently used in the clinic, docetaxel is always more active than paclitaxel (from 1.1 to 3.4 fold). SB-T-1250 and SB-T-1213 showed a striking effect against all cell lines, exhibiting substantially higher potencies than that of paclitaxel (from 1.8 to 69-fold for SB-T-1250, and from 3 to 412-fold for SB-T-1213).

TABLE 4

$IC_{50}$ Values (expressed in nM) against a panel of human cancer cell lines

| Drug | A2780 | MCF-7 wt | MCF-7 ADRr | WiDr | PC-3 | DU-145 | NCI-H23 |
|---|---|---|---|---|---|---|---|
| Paclitaxel | 5.4 | 5.8 | 3300 | 3.8 | 3.4 | 1.5 | 4.1 |
| Docetaxel | 4.95 | 3.6 | 970 | 2.3 | 1.8 | 0.8 | 3 |
| SB-T-1250 | 3.03 | 2.3 | 48 | 0.5 | 0.7 | 0.6 | 1.6 |
| SB-T-1213 | 1.77 | 0.9 | 8 | 0.4 | 0.3 | 0.3 | 0.7 |

In Vivo Testing

The efficacy of the test compounds on solid tumors in vivo was determined experimentally according to the following general experimental protocol:

The mice subjected to the experiment were subcutaneously grafted bilaterally with 30 to 60 mg of a tumor fragment on day zero. Mice bearing tumors were mixed before being subjected to the various treatments and controls. In the case of treatment of advanced tumors, tumors were allowed to develop to the desired size, and mice having insufficiently developed tumors were eliminated. The selected mice were distributed at random to undergo the treatments and controls. Mice not bearing tumors may also be subjected to the same treatments as the tumor-bearing mice in order to be able to dissociate the toxic effect from the specific effect on the tumor. Chemotherapy generally began from 3 to 22 days after grafting, depending on the type of tumor, and the mice were observed every day. The different mice groups were weighed 3 or 4 times a week until the maximum weight loss was attained (nadir), and the groups were then weighed at least once a week until the end of the trial.

The tumors were measured 2 or 3 times a week until the tumor reached approximately 2 grams, or until the animal died, if this occurred before the tumor reached 2 grams. The mice were autopsied when sacrificed.

The antitumor activity was determined in accordance with different parameters recorded such as dose (mg/kg), mode of administration, time of administration, cytotoxicity, toxicity and $\log_{10}$ cell kill.

The results obtained in the treatment of model systems for mammary cancer, melanoma, and docetaxel-resistant melanoma with an oral formulation of SB-T-1213, and with intravenous formulations of SB-T-1213, SB-T-121303, SB-T-121304, and SB-T-1250 are reported below and shown in Table 5.

EXAMPLE 54

Oral Administration of SB-T-1213 to MA17/A Tumor-Bearing Mice

SB-T-1213 was evaluated in C3H/HeN female mice bearing mammary adenocarcinoma MA17/A with an intermittent schedule of oral administrations. The compound for administration was formulated in 10% ethanol, 10% polysorbate 80, and 80% glucose/5% water.

SB-T-1213 was administered 3 times a day on 3 and 7 days post tumor implantation. The two highest dosages of 36.4 and 22.6 mg/kg/adm. were toxic, producing 5/5 drug related deaths (DD) and 20% body weight loss, respectively. However, the highest nontoxic dose of 14 mg/kg/adm. (total dose of 84 mg/kg), produced 8.4% body weight loss at nadir, 4 days post therapy. This highest nontoxic dose was found highly active, with a $\log_{10}$ cell kill of greater than 3. One of five mice was a tumor-free survivor (TFS) on day 94 post tumor implantation with this dosage. Two lower dosages of 8.7 and 5.4 mg/kg/adm. also maintained activity, having a $\log_{10}$ cell kill of greater than 3 and of 2.5, respectively.

EXAMPLE 55

Intravenous Administration of Taxoids to Female Mice Bearing B16 Melanoma

SB-T-1213, SB-T-121303, SB-T-121304 and SB-T-1250 were evaluated in B6D2F1 female mice bearing B16 melanoma. The general experimental protocol was as described above. The compounds evaluated were administered intravenously (iv) on an intermittent schedule on days 3, 5, and 7 post tumor implantation. With the exception of SB-T-1250, solutions of the compounds for administration were prepared in 5% ethanol, 5% polysorbate 80, and 90% glucose 5% water. In order to overcome solubility problems, SB-T-1250 was formulated in 5% DMSO, 5% polysorbate 80, and 90% glucose 5% in water.

SB-T-1213 at the highest administered dosage of 19 mg/kg/adm., was found to be toxic, producing 1/5 drug related deaths (DD). However, the highest nontoxic dose of 11.8 mg/kg/adm. (total dose of 35.4 mg/kg) was highly active, generating a $\log_{10}$ cell kill of 3. This highest nontoxic dose produced 15.3% body weight loss at nadir, 3 days post therapy. Two lower dosages of 7.3 and 4.5 mg/kg/adm. maintained activity, with a $\log_{10}$ cell kill of 1.8 and 1.6, respectively.

SB-T-121303 was toxic at the two highest administered dosages, with 100% DD at 5.4 and 3.2 mg/kg/adm. However, the highest nontoxic dose of 1.9 mg/kg/adm. (total dose of 5.7 mg/kg) was active, with a $\log_{10}$ cell kill of 1.7. The highest nontoxic dose produced a 16.9% body weight loss at nadir, 13 days post therapy. The lower dosage of 1.2 mg/kg/adm. was inactive (T/C=64%).

SB-T-121304 was found to be toxic at the three highest administered dosages, producing 100% DD at 5.4 and 3.2 mg/kg/adm. and 3/5 DD at 1.9 mg/kg/adm. However, the highest nontoxic dose of 1.2 mg/kg/adm. (total dose of 3.6 mg/kg) was found active, with a $\log_{10}$ cell kill of 0.9, and a 1.5% body weight loss at nadir, 10 days post last treatment.

SB-T-1250 was toxic at the three highest administered dosages, producing 100% DD at 19 mg/kg/adm., 3/5 DD at 11.8 mg/kg/adm. and 1/5 DD at 7;3 mg/kg/adm. The highest nontoxic dose of 4.5 mg/kg/adm., total dose of 13.5 mg/kg, produced 12.5% body weight loss at nadir, 3 days post last treatment, and was found active (T/C=23%, 1.2 $\log_{10}$ cell kill).

EXAMPLE 56

Intravenous Administration of Taxoids to B16/TXT Melanoma-bearing Mice

SB-T-1213, SB-T-121303, SB-T-121304 and SB-T-1250 were evaluated in B6D2F1 female mice bearing the docetaxel-resistant melanoma, B16/TXT. The general experimental protocol was as described above. The compounds evaluated were administered intravenously on an intermittent schedule on days 3, 5, and 7 post tumor implantation.

SB-T-1213 was active at the highest administered dosage of 19 mg/kg/adm. (total dose of 57 mg/kg). This active dosage produced 17.1% body weight loss at nadir, 4 days post therapy, and showed a $\log_{10}$ cell kill of 1.6. Two lower dosages of 11.8 and 7.3 mg/kg/adm. also had activity, with a $\log_{10}$ cell kill of 1 for both dosages. The lowest tested dosage of 4.5 mg/kg/adm. was inactive (T/C=74%).

SB-T-121303 was found toxic at the two highest administered dosages, producing 100% drug related deaths (DD) at 3.2 mg/kg/adm. and 1/5 DD at 1.9 mg/kg/adm. The highest nontoxic dose of 1.2 mg/kg/adm., total dose of 3.6 mg/kg, produced 12.5% body weight loss at nadir, 13 days post therapy, and was found active (T/C=38%, 1.5 log cell kill). The lower dosage of 0.7 mg/kg/adm. was inactive (T/C=94%).

SB-T-121304 was found toxic at the two highest administered dosages, producing 100% DD at 3.2 mg/kg/adm. and 4/5 DD at 1.9 mg/kg/adm. The highest nontoxic dose of 1.2 mg/kg/adm., total dose of 3.6 mg/kg, produced 13.6% body weight loss at nadir, 12 days post last treatment, and was found active (T/C=32%, 1.1 $\log_{10}$ cell kill). The dosage below of 0.7 mg/kg/adm. was inactive (T/C=78%).

SB-T-1250, administered in the DMSO formulation previously described, was found toxic at the highest administered dosage of 11.8 mg/kg/adm. with 5/5 (100%) DD. However, the highest nontoxic dose of 7.3 mg/kg/adm. (total dose of 21.9 mg/kg) was active, with a $\log_{10}$ cell kill of 1.1. This highest nontoxic dose produced 16.7% body weight loss at nadir, 4 days post last treatment. Two lower dosages of 4.5 and 2.8 mg/kg/adm. were inactive (T/C=108% and 152%, respectively).

Table 5 below reports the results for all active dosage of the compounds tested.

TABLE 5

Taxoid Administration at Various Dosages in Cancer Model Systems

| | | Treatment | | | Therapeutic Response | | | |
|---|---|---|---|---|---|---|---|---|
| Agent (route of administration) | Tumor (implantation site) | Dose mg/kg/adm | Schedule (days) | Total dose mg/kg | % body weight loss at nadir (day of nadir) | T/C % | $\log_{10}$ cell kill | Responses (TFS) |
| SB-T-1213 (po) | MA17/A | 14.0 | 3, 7 | 84.0 | 8.4 (4) | 0 | >3.0 | (1/5) HA |
| | | 8.7 | | | | | >3.0 | (1/5) A |
| | | 5.4 | | | | | 2.5 | A |
| SB-T-1213 (iv) | B16 | 11.8 | 3, 5, 7 | 35.4 | 15.3 (3) | 0 | 3 | HA |
| | | 7.3 | | | | | 1.8 | A |
| | | 4.5 | | | | | 1.6 | A |

TABLE 5-continued

Taxoid Administration at Various Dosages in Cancer Model Systems

| Agent (route of administration) | Tumor (implantation site) | Treatment | | | Therapeutic Response | | | |
|---|---|---|---|---|---|---|---|---|
| | | Dose mg/kg/adm | Schedule (days) | Total dose mg/kg | % body weight loss at nadir (day of nadir) | T/C % | $\log_{10}$ cell kill | Responses (TFS) |
| SB-T-121303 (iv) | B16 | 1.9 | 3, 5, 7 | 5.7 | 16.9 (13) | 12 | 1.7 | A |
| SB-T-121304 (iv) | B16 | 1.2 | 3, 5, 7 | 3.6 | 1.5 (10) | 33 | 0.9 | A |
| SB-T-1250 (iv) | B16 | 4.5 | 3, 5, 7 | 13.5 | 12.5 (3) | 23 | 1.2 | A |
| SB-T-1213 (iv) | B16/TXT | 19 | 3, 5, 7 | 57 | 17.1 (4) | 11 | 1.6 | A |
| | | 11.8 | | | | | 1 | A |
| | | 7.3 | | | | | 1 | A |
| SB-T-121303 (iv) | B16/TXT | 1.2 | 3, 5, 7 | 3.6 | 12.5 (13) | 38 | 1.5 | A |
| SB-T-121304 (iv) | B16/TXT | 1.2 | 3, 5, 7 | 3.6 | 13.6 (12) | 32 | 1.1 | A |
| SB-T-1250 (iv) | B16/TXT | 7.3 | 3, 5, 7 | 21.9 | 16.7 (4) | 41 | 1.1 | A |

Abbreviations used: TFS = tumor free survivors; CTI = combination toxicity; iv = intravenous; po = by mouth; A = active; HA = highly active. Tumor types are as described in the Examples.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of formula:

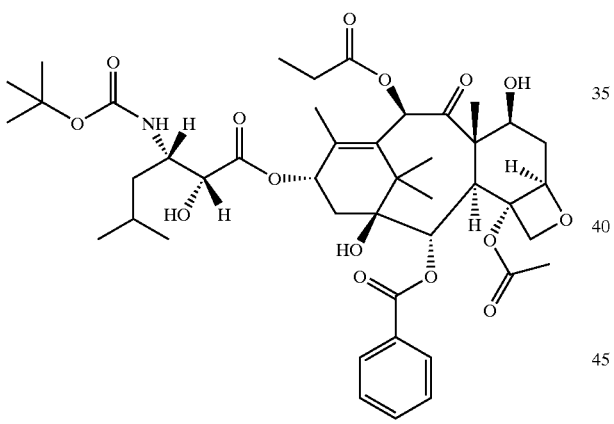

wherein the compound is in free form or in pharmaceutically acceptable salt form.

2. A pharmaceutical composition comprising an effective amount of a compound as claimed in claim 1, and a pharmaceutically acceptable carrier.

3. The pharmaceutical composition of claim 2, wherein said carrier is appropriate for oral administration.

4. A method for treating cancer, comprising orally administering to a patient in need thereof an effective amount of a compound as claimed in claim 1.

5. The method of claim 4, wherein said cancer is at least one of colon, breast, ovary, and skin.

6. The method of claim 5, wherein said cancer is resistant to at least one of paclitaxel and docetaxel.

7. A compound of formula:

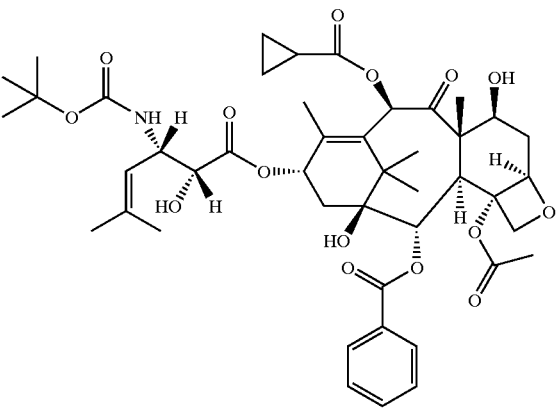

wherein the compound is in free form or in pharmaceutically acceptable salt form.

8. A pharmaceutical composition comprising an effective amount of a compound as claimed in claim 7, and a pharmaceutically acceptable carrier.

9. The pharmaceutical composition of claim 8, wherein said carrier is appropriate for oral administration.

10. A method for treating cancer, comprising orally administering to a patient in need thereof an effective amount of a compound as claimed in claim 7.

11. The method of claim 10, wherein said cancer is at least one of colon, breast, ovary, and skin.

12. The method of claim 11, wherein said cancer is resistant to at least one of paclitaxel and docetaxel.

13. A compound of formula:

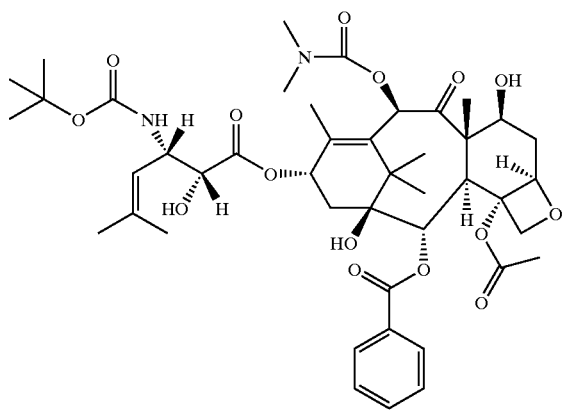

wherein the compound is in free form or in pharmaceutically acceptable salt form.

14. A pharmaceutical composition comprising an effective amount of a compound as claimed in claim 13, and a pharmaceutically acceptable carrier.

15. The pharmaceutical composition of claim 14, wherein said carrier is appropriate for oral administration.

16. A method for treating cancer, comprising orally administering to a patient in need thereof an effective amount of a compound as claimed in claim 13.

17. The method of claim 16, wherein said cancer is at least one of colon, breast, ovary, and skin.

18. The method of claim 17, wherein said cancer is resistant to at least one of paclitaxel and docetaxel.

* * * * *